United States Patent [19]

Alig et al.

[11] Patent Number: 5,663,297

[45] Date of Patent: Sep. 2, 1997

[54] ANTITHROMBIC PEPTIDES

[75] Inventors: Leo Alig, Kaiseraugst; Albrecht Edenhofer, Riehen; Marcel Müller, Frenkendorf, all of Switzerland; Arnold Trzeciak, Schopfheim, Germany; Thomas Weller, Basel, Switzerland

[73] Assignee: Hoffmann-La Roche Inc., Nutley, N.J.

[21] Appl. No.: 454,453

[22] Filed: May 30, 1995

Related U.S. Application Data

[63] Continuation of Ser. No. 275,097, Jul. 14, 1994, abandoned, which is a continuation of Ser. No. 673,929, Mar. 25, 1991, abandoned, which is a division of Ser. No. 481,846, Feb. 20, 1990, abandoned.

[30] Foreign Application Priority Data

| | | | |
|---|---|---|---|
| Feb. 23, 1989 | [CH] | Switzerland | 669/89 |
| Nov. 29, 1989 | [CH] | Switzerland | 4265/89 |

[51] Int. Cl.$^6$ .................................... A61K 38/06
[52] U.S. Cl. ............... 530/331; 546/224; 546/227; 546/233; 562/571
[58] Field of Search ............... 514/17, 18, 19; 530/331; 546/224, 227, 233; 562/571

[56] References Cited

U.S. PATENT DOCUMENTS

| | | | |
|---|---|---|---|
| 4,055,636 | 10/1977 | Okamoto et al. | 424/177 |
| 4,578,079 | 3/1986 | Ruoslahti | 623/11 |
| 4,683,291 | 7/1987 | Zimmerman | 530/324 |
| 4,857,508 | 8/1989 | Adams et al. | 514/18 |
| 5,039,805 | 8/1991 | Alig et al. | 546/224 |
| 5,061,693 | 10/1991 | Nutt et al. | 514/17 |

FOREIGN PATENT DOCUMENTS

| | | |
|---|---|---|
| 0275748 | 7/1988 | European Pat. Off. |
| 2655636 | 6/1977 | Germany |

OTHER PUBLICATIONS

Pierschbacher et al., J. of Bio. Chem., 262:17294–17298 (1987).
Turner et al., Biochemistry, 25:4929–4935 (1986).
Okamoto et al., Chem. Abstract, 89: No. 60043,589 (1978).
Steiner et al., J. Bio. Chem., 264:13102–13108 (1989).
Cook et al., Tips, 11:444–451 (Nov. 1990).
Saiki et al, Br. J. Cancer, 60:722–828 (1989).
Saiki et al., Jpn. J. Cancer Res. 81:660–667 (Jun./Jul. 1990).
Knudsen et al., Experimental Cell Research 179:42–49 (1988).
Pharmazie, 39:80–86 (1984).
Vieweg et al., Pharmazie 39(2):82–86 (1984).
Spatola, Chemistry and Biotechnology of Amino Acids, Peptides and Proteins, Weinstein ed. (Marcell Dekker Inc. 1983) pp. 267–357.
Vieweg, Pharmazie 39, 82–86, 1984.

*Primary Examiner*—Cecilia J. Tsang
*Assistant Examiner*—David Lukton
*Attorney, Agent, or Firm*—George W. Johnston; Patricia S. Rocha-Tramaloni; Raina Semionow

[57] ABSTRACT

Disclosed herein are peptide of the formula $$R-CONH-CH_2-CONH-CH(R')-CH_2COOH \qquad I$$

wherein R and R' are as defined herein. The claimed peptide derivatives inhibit platelet aggregation and as such are useful in the treatment of thrombosis.

21 Claims, No Drawings

ANTITHROMBIC PEPTIDES

This is a continuation, of application Ser. No. 08/275,097, filed Jul. 14, 1994, now abandoned, which is a continuation of Ser. No. 07/673,929, filed Mar. 25, 1991, now abandoned which is a division of Ser. No., 07/481,846, filed Feb. 20, 1990 now abandoned.

FIELD OF THE INVENTION

The present invention is concerned with novel glycine derivatives, a process for their manufacture, pharmaceutical preparations which contain such glycine derivatives as well as the use of the glycine derivatives in the manufacture of pharmaceutical preparations.

SUMMARY OF THE INVENTION

The novel glycine derivatives are compounds of the formula $$R\text{—CONH—CH}_2\text{—CONH—CH(R')—CH}_2\text{COOH} \qquad I$$

wherein R is a group of the formula

  (R-1)

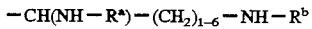  (R-2)

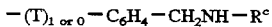  (R-3)

or

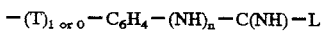  (R-4)

and $R^a$ is hydrogen, —COO—$C_{1-4}$-alkyl, Z, —COC$_6$H$_5$, —COC$_6$H$_4$N$_3$, —SO$_2$C$_6$H$_5$, —SO$_2$-naphthyl or —COCH$_2$N(Y)—CH$_2$CH$_2$NH—Y, Y is hydrogen, Boc or Z, $R^b$ is a group of the formula —C(NH)(CH$_2$)$_{0-3}$—CH$_3$ or

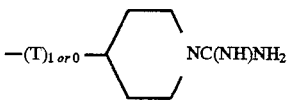

or, where $R^a$ is a group of the formula
—COC$_6$H$_4$N$_3$, —SO$_2$C$_6$H$_5$, SO$_2$-naphthyl or
—COCH$_2$N(Y)—CH$_2$CH$_2$NH—Y, $R^b$ is also amidino, $R^c$ is hydrogen or amidino, n is the number 1 or 0, L is amino or, where n is the number 1, L is also
—(CH$_2$)$_{0-3}$ CH$_3$, T is a group of the formula —CH$_2$—(O)$_{1\ or\ 0}$—,
—CH=CH—, —CH(R$^d$)—CH$_2$— or —CH$_2$CO—,
whereby a carbonyl group present in the group T can also be present as a ketal, $R^d$ is hydrogen or —NH—R$^a$, R' is hydrogen or —CO—R$^o$, $R^o$ is amino, —NH—$C_{1-4}$-alkyl, —NH(CH$_2$)$_{1-4}$—C$_6$H$_5$, —NH(CH$_2$)$_{1-4}$—C$_6$H$_4$-Hal, —NH—C$_6$H$_4$—COOH, —NH—C$_6$H$_4$—COO—$C_{1-4}$-alkyl or an α-amino-carboxylic acid attached via the amino group, as well as hydrates or solvates and physiologically usable salts thereof. The glycine derivatives of the present invention inhibit the binding of adhesive proteins to blood platelets as well as blood platelet aggregation and cell-cell adhesion.

DETAILED DESCRIPTION OF THE INVENTION

In the scope of the present invention Me denotes methyl, Bzl denotes benzyl, tBu denotes t-butyl, Hal denotes one of the 4 halogens, Boc denotes t-butoxy-carbonyl, Z denotes benzyloxycarbonyl, Ac denotes acetyl, Su denotes succinimide, Fmoc denotes 9H-fluoren-9yl-methoxycarbonyl, Arg denotes L-arginyl, Orn denotes L-ornithyl, Val denotes L-valyl, Phe denotes L-phenyl-alanyl, Leu denotes L-leucyl, Ile denotes L-isoleucyl, Lys denotes lysyl, Ser denotes L-seryl, Thr denotes L-threonyl, Gly denotes glycyl, Ala denotes L-alanyl, Asp denotes L-α-aspartyl, Aeg denotes N-(2-aminoethyl)-glycyl and Nal (1) denotes 3-(1-naphthyl)-L-alanyl.

Examples of α-aminocarboxylic acids attached via the amino group are Val, Phe, Leu, Ile, Ser, Thr, Nal(1), N-isopropyl-Gly, β-cyclohexyl-Ala and cycloleucine.

The compounds of formula I can be solvated, especially hydrated. The hydration can be effected in the course of the manufacturing process or can occur gradually as a consequence of hygroscopic properties of an initially anhydrous compound of formula I.

Examples of physiologically usable salts of the compounds of formula I are salts with physiologically compatible mineral acids such as hydrochloric acid, sulphuric acid or phosphoric acid or with organic acids such as methane-sulphonic acid, acetic acid, trifluoroacetic acid, citric acid, fumaric acid, succinic acid or salicylic acid. The compounds of formula I can also form salts with physiologically compatible bases. Examples of such salts are alkali metal, alkaline earth metal, ammonium and alkylammonium salts such as the Na, K, Ca or trimethylammonium salt. Compounds of formula I which contain an amino, amidino or guanidino group can also be present in the form of zwitterions.

The compounds of formula I which contain one or more asymmetric C atoms can be present as enantiomers, as diastereomers or as mixtures thereof, e.g. as racemates.

Preferred compounds of formula I are those in which R—CO— represents the group Aeg-Arg-, Z-Aeg(Z)-Arg-, 2-naphthyl-SO$_2$-Arg-, o-azidobenzoyl-Arg-, N$_2$-Boc-N$_6$-(1-iminoethyl)-Lys-, N$_2$-Boc-N$_5$-(3a,4,5,6,7,7a-hexahydro-3a, 7a-dihydroxy-1H-benzimidazol-2-yl)-Orn-, p-(aminomethyl)hydrocinnamoyl, p-amidinohydrocinnamoyl, 3-(p-amidinophenyl or p-guanidinophenyl)-alanyl, N—Z— or N-Boc-3-(p-amidinophenyl)alanyl, N-Boc-3-(p-guanidinophenyl)alanyl, p-amidinophenoxyacetyl or p-amidinophenacetyl.

Further, the compounds of formula I in which R' is hydrogen, —CO-Val-OH, —CO-Ser-OH, —CO-Phe-OH, 1-carboxy-2-(1-naphthyl)ethylidenecarbamoyl, —CO-Ile-OH, carboxyphenylcarbamoyl, isobutylcarbamoyl or p-fluorophenethylcarbamoyl are preferred.

The following compounds are especially preferred:

[3-(p-Amidinophenyl)-DL-alanyl]-Gly-Asp-Val-OH,
Z-Aeg(Z)-Arg-Gly-Asp-Val-OH,
Aeg-Arg-Gly-Asp-Val-OH,
Aeg Arg-Gly-Asp-Ser-OH,
N-Aeg-Arg-Gly-Asp-Nal(1)-OH,
Aeg-Arg-Gly-Asp-Ile-OH,
[N$_2$-Boc-N$_6$-(1-iminoethyl)-L-lysyl]-Gly-Asp-Val-OH,
N-[(o-azidobenzoyl)-Arg-Gly-Asp]-anthranilic acid, N$_2$-Boc-N$_5$-(3a,4,5,6,7,7a-hexahydro-3a,7a-dihydroxy-1H-benzimidazol-2-yl)-L-ornithyl]-Gly-Asp-Val-OH,
[N-Boc-3-(p-guanidinophenyl)-DL-alanyl]-Gly-Asp-Val-OH,
[3-(p-amidinophenyl)-DL-alanyl]-Gly-Asp-Nal(1)-OH,
[N-Boc-3-(p-amidinophenyl)-DL-alanyl]-Gly-Asp-Val-OH,
(p-amidinohydrocinnamoyl)-Gly-Asp-Nal(1)-OH,
[3-(p-amidinophenyl)-D-alanyl]-Gly-Asp-Val-OH,
(p-aminomethylhydrocinnamoyl)-Gly-Asp-Val-OH,
(p-amidinohydrocinnamoyl)-Gly-Asp-Val-OH,
[3-(p-amidinophenyl)-L-alanyl]-Gly-Asp-Val-OH,
(p-amidinophenoxy)acetyl-Gly-Asp-Val-OH and
(p-amidinophenyl)acetyl-Gly-Asp-Val-OH.

The compounds of the present invention can be manufactured in a manner known per se by:

a) cleaving off the ester group(s) present and one or more protected amino, amidino or guanidino groups present from a compound of the formula $$R^2\text{—CONH—CH}_2\text{—CONH—CH}(R^4)\text{—CH}_2\text{COOR} \quad \text{II}$$

wherein R$^2$ is a group of the formula

$$-\text{CH}(\text{NH}-R^a)-(\text{CH}_2)_{1-6}-R^5 \quad \text{(R-1a)}$$

$$-(T)_{1 \text{ or } 0}-C_6H_4-CH_2-R^6 \quad \text{(R-2a)}$$

$$-(T)_{1 \text{ or } 0}-C_6H_4-R^7 \quad \text{(R-3a)}$$

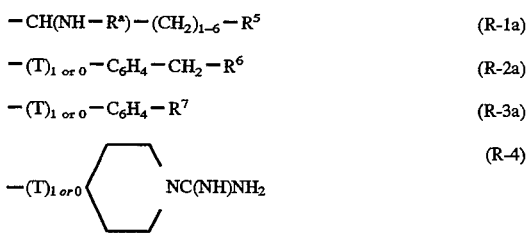

in which
R$^5$ is a protected guanidino group or a group —NH—R$^b$,
R$^6$ is a protected amino or guanidino group or a group —NH—R$^c$,
R$^7$ is optionally protected amidino or guanidino,
R$^3$ is hydrogen or a readily cleavable ester group,
R$^4$ has the same significance as R' or is a group —COR$^8$ in which R$^8$ is a readily cleavable α-aminocarboxylic acid ester attached via the amino group,
with the proviso that R$^2$ must contain at least one protected guanidino, amino or amidino group R$^5$, R$^6$ or R$^7$ and must not be a group of the formula R-4 where R$^3$ is hydrogen and R$^4$ has the same significance as R',
and R$^a$, R$^b$, R$^c$, R' and T have the above significance,
or b) reacting an amine of the formula

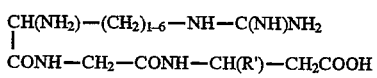

with an agent which introduces the group —COC$_6$H$_5$, —SO$_2$C$_{65}$, —SO$_2$-naphthyl or —COCH$_2$N(Y)—CH$_2$CH$_2$NH—Y, wherein R' and Y have the above significance, or c) reacting an amine of the formula

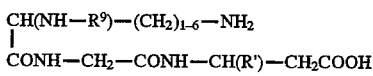

wherein
R$^9$ is —COO—C$_{1-4}$-alkyl, Z, —COC$_6$H$_5$, —COC$_6$H$_4$N$_3$, —SO$_2$C$_6$H$_5$, —SO$_2$-naphthyl or —COCH$_2$N(Y')—CH$_2$CH$_2$NH—Y , in which Y' represents Boc or Z and R' has the above significance, with an agent which introduces the group —C(NH)(CH$_2$)$_{0-3}$—CH$_3$, or d) reacting a guanidine derivative of the formula

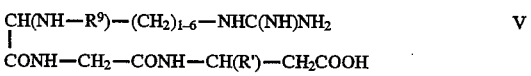

wherein R' and R$^9$ have the above significance, with 1,2-cyclohexanedione, or e) converting the amino group in an amine of formula IV or an amine of the formula

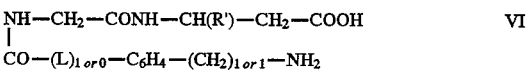

wherein L is a group —CH$_2$(O)$_{1 \text{ or } 0}$—, —CH=CH— or —CH(NH—R$^9$)—CH$_2$— and R' and R' have the above significance,
into a guanidino group, or f) hydrogenating a nitrile of the formula

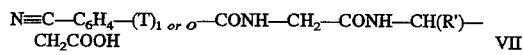

to the amine, g) if desired, functionally modifying a reactive substituent present in the group R of a compound of formula I, and h) if desired, converting a compound of formula I into a salt or converting a salt of a compound of formula I into the free compound of formula I.

Examples of protected amino, amidino and guanidino groups are —NH—Z and —NH-Boc, —C(NH)NH—Z; —NHC(NH)NH—NO$_2$, —NHC(N-Boc)—NH-Boc and —NHC(N—Z)—NH—Z. Examples of readily cleavable ester groups COOR$^3$ are methoxycarbonyl, t-butoxycarbonyl and benzyloxycarbonyl. Examples of a residue R$^8$ are -Val-OtBu, -Val-OBzl and -Ser(tBu)-OtBu.

The cleavages according to process variant a) can be carried out in a manner known per se. Thus, ester groups such as t-butoxycarbonyl can be cleaved off with an acid such as formic acid, trifluoroacetic acid (TFA) or hydrochloric acid in a solvent such as methylene chloride, tetrahydro- furan (THF) or ethyl acetate at a temperature up to about 40° C., preferably between about 0° C. and room temperature. Amino, guanidino or amidino protecting groups such as Boc which are present in the substituent R$^2$ are thereby simultaneously cleaved off. In this manner compounds of formula II which are obtained by solid-phase synthesis can also be removed from the carrier, e.g. a styrene-1% divinylbenzene resin containing p-benzyloxybenzyl alcohol residues.

Ester groups such as methoxycarbonyl can be saponified with a base such as an alkali metal hydroxide, e.g. sodium hydroxide, in a solvent such as acetone at a temperature up to about 40° C., preferably at room temperature. Benzyl esters can be cleaved by hydrogenation in the presence of a noble metal catalyst such as palladium-on-carbon (Pd/C) in a solvent such as methanol, ethanol, formic acid or acetic acid at a temperature up to about 40° C., preferably at room temperature. Amino or amidino protecting groups such as Z; or guanidino protecting groups such as NO$_2$ and Z which are present in the group R$^2$ are thereby simultaneously cleaved off.

Variant b) can also be carried out in a manner known per se. For the introduction of the —COC$_6$H$_4$N$_3$ group, a compound of formula III can be reacted with pyridine hydrochloride in the presence of a base such as N-ethyldiisopropylamine (DIPEA) and of 1,1,3,3-tetramethyl-2-[4-oxo-1,2,3benzotriazin-3(4H)-yl]uronium the hexafluorophosphate (HOBTU) in a solvent such as DMF. For the introduction of a —SO$_2$-naphthyl group, a compound of formula III can be treated e.g. with naphthalene-2-sulphonyl chloride and a base such as NaHCO$_3$ in a solvent such as acetone and water. For the introduction of a —COCH$_2$N(Y)—CH$_2$CH$_2$NH—Y group, a compound of formula III can be reacted e.g. with Z-Aeg (Z)-OSu in the presence of a base such as pyridine hydrochloride in a solvent such as DMF. These reactions are conveniently carried out at a temperature up to about 40° C., preferably at room temperature.

Examples of agents which introduce a group —C(NH)—(CH$_2$)$_{0-3}$—CH$_3$ are ethers of the formula MeOC(NH)—(CH$_2$)$_{0-3}$—CH$_3$, e.g. methyl acetimidate. The reaction according to variant c) can be carried out e.g. using the hydrochloride of such an ether in the presence of a base such as sodium hydroxide in a solvent such as water at a temperature up to about 40° C., preferably at room temperature.

The reaction according to variant d) can be carried out in a sodium borate buffer under an inert atmosphere such as argon at a temperature up to about 40° C., preferably at room temperature.

Variant e) can be carried out by reacting the amine of formula VI in a solvent such as water with a base, e.g. potassium carbonate, and aminoiminomethanesulphonic acid at a temperature up to about 40° C., preferably at room temperature.

Variant f) can be carried out by hydrogenating the nitrile of formula VII in an alcoholic, e.g. a methanolic, ammonia solution in the presence of a catalyst such as Raney-nickel at a temperature up to about 40° C., preferably at room temperature.

The functional modification according to variant g) can also be carried out according to familiar methods. Thus, the protecting groups can be cleaved off from a protected group R—CO— such as Z-Aeg(Z)-Arg or N-Boc-3-(p-amidinophenyl)-D,L-alanyl, e.g. as described above in connection with variant a).

A primary amino group which is present in a substituent R can be converted into the —NH-Boc group, e.g. by means of di-t-butyl dicarbonate in a solvent such as DMF in the presence of a base such as triethylamine at a temperature up to about 40° C., preferably at room temperature.

The compounds of formula II are novel and are also an object of the invention. Their preparation can be effected starting from known compounds according to methods which are known per se and which are familiar to a person skilled in the art. Thus, amidines of formula II in which R$^2$ is a group —(T)$_{1\ or\ o}$—C$_6$H$_4$—C(NH)NH$_2$ can be prepared starting from the corresponding nitriles of the formula

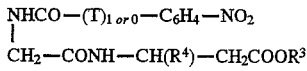

via the corresponding thioamides and S-methylimino esters. For example, the nitrile VIII can be reacted with hydrogen sulphide and triethylamine in pyridine and the thioamide obtained can be reacted with methyl iodide in acetone and subsequently with ammonium acetate in methanol.

A guanidine derivative of formula II in which R$^2$ is a group of the formula —(T)$_1$ or $_o$—C$_6$H$_4$—NHC(NH)NH$_2$ can be prepared starting from the corresponding nitro compound of the formula

via the corresponding primary amine and the corresponding guanidine derivative which is protected by nitro. Thus, the nitro compound IX can be hydrogenated in the presence of Pd/C to give the primary amine, the latter can be reacted with 3,5-dimethyl-N-nitro-1H-pyrazole-1-carboxamidine in ethanol and the nitro group can be cleaved off by hydrogenation in the presence of Pd/C in acetic acid.

A compound of formula II which is bonded to a carrier can be prepared by solid-phase synthesis in a manner known per se. Thus, a suspension of a carrier consisting of a styrene-divinylbenzene resin containing p-benzyloxybenzyl alcohol residues in DMF can be treated with N-(9H-fluoren-9-ylmethoxycarbonyl)-3-(1-naphthyl)-L-alanine, then with 2-(1H-benzotriazol-1-yl)-1,1,3,3-tetramethyluronium hexafluorophosphate (HBTU), 4-dimethylaminopyridine and DIPEA. The free hydroxy groups can be acetylated with acetic anhydride in the presence of DIPEA in DMF. Subsequently, the individual protected amino acids such as Fmoc-Asp(OtBu)-OH, Fmoc-Gly-OH, Fmoc-Arg-OH.HCl and Boc-Aeg(Boc)-OSu can be coupled in succession to a compound of the formula Boc-Aeg(Boc)-Arg-Gly-Asp(OBut)-Nal(1)-O-carrier e.g. according to the reaction protocol given in Example 10.

Acids of formula III such as. H-Arg-Gly-Asp-Val-OH and H-Arg-Gly-Asp-Ser-OH are know or can be prepared in a manner known per se, e.g. by reacting a corresponding ester of the formula

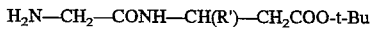

with Z-Arg(Z$_2$)-OSu, cleaving the ester group and removing the arginine protecting groups which are present in the thus-obtained product by catalytic hydrogenation in methanol in the presence of Pd/C.

An amine of formula IV, e.g. one in which R' is the group —CO-Val-OH and R$^9$ is a group —COO—C$_{1-4}$-alkyl, can be prepared starting from the corresponding diester, e.g. H-Gly-Asp(OBzl)-Val-OBzl via the lysine derivative Boc-Lys(Z)-Gly-Asp(O-Bzl)-Val-OBzl. Thus, the diester referred to can be reacted with Boc-Lys(Z)-OSu in DMF in the presence of N-methylmorpholine and the lysine derivative obtained can be catalytically hydrogenated to the corresponding amine of formula IV, Boc-Lys-Gly-Asp-Val-OH.

A guanidine derivative V, e.g. one in which R$^9$ is a group —COO—C$_{1-4}$-alkyl can be prepared by reacting the corresponding compound of formula III with di-t-butyl dicarbonate in the presence of pyridine hydrobromide in aqueous dioxan.

An amine of formula VI, e.g. Boc-D,L-Phe(p-NH$_2$)-Gly-Asp-Val-OH can be prepared starting from a corresponding diester, e.g. H-Gly-Asp(OBzl)-Val-OBzl.TFA via the nitro compound Boc-D,L-Phe(p-NO$_2$)-Gly-Asp(OBzl)-Val-OBzl. Thus, the diester referred to can be treated with Boc-D,L-Phe(p-NH$_2$)-OH in DMF in the presence of HBTU and DIPEA and the nitro compound obtained can be catalytically hydrogenated to the desired amine.

A nitrile VII, e.g. one in which R' is the group —CO-Val-OH, can be prepared by coupling a corresponding diester, e.g. H-Gly-Asp(OtBu)-Val-OtBu, and a corresponding nitrile such as p-cyanohydrocinnamic acid to give p-cyanohydrocinnamoyl-Gly-Asp(OtBu)-Val-OtBu and acidolysis of the latter.

A nitrile of formula VIII, e.g. one in which $R^4$ is the group —CO-Ser(tBu)-OtBu, can be prepared by coupling a corresponding diester, e.g. H-Gly-Asp(OtBu)-Ser(tBu)-OtBu, with rac-Z-(p-cyanophenyl)alanine in DMF under argon in the presence of N-methylmorpholine and HBTU.

Analogously, a diester such as H-Gly-Asp(OtBu)-Val-OtBu can be coupled with Boc-Phe(4-NO$_2$)-OH to give the corresponding nitro compound IX, e.g. [N-Boc-3-(p-nitrophenyl)-L-alanyl]-Gly-Asp(OtBu)-Val-OtBu.

A compound of formula X, e.g. N-[H-Gly-Asp(OtBu)]-anthranilic acid, can be prepared by coupling Z-Asp(OtBu)-OH and benzyl anthranilate.tosylate in DMF with 1,1,3,3-tetramethyl-2-[4-oxo-1,2,3-benzotriazin-3(4H)-yl]uronium tetrafluoroborate (TOBTU) and DIPEA, cleaving the Z group from the ester obtained, coupling the resulting compound, N-[H-Asp(OtBu)]-anthranilic acid, with Z-Gly-OSu and removing the Z group from the resulting product by hydrogenation.

A diester starting material such as H-Gly-Asp(OBzl)-Val-OBzl.TFA can be prepared by coupling Boc-Asp(OBzl)-OH with H-Val-OBzl.tosylate in the presence of N-methylmorpholine and isobutyl chloroformate in DMF, acidolyzing the resulting Boc-Asp(OBzl)-Val-OBzl with TFA, coupling the resulting H-Asp(OBzl)-Val-OBzl.TFA with Boc-Gly-OSu and N-methylmorpholine in ethyl acetate and subsequently acidolyzing.

A diester such as H-Gly-Asp(OtBu)-Nal(1)-OMe can be prepared by coupling Z-Gly-OH with H-Asp(OtBu)-OMe, saponifying the resulting Z-Gly-Asp(OtBu)-OMe with sodium hydroxide in acetone, coupling the resulting Z-Gly-Asp(OtBu)-OH with H-Nal(1)-OMe and hydrogenolyzing the resulting Z-Gly-Asp(OtBu)-Nal(1)-OMe.

A diester such as H-Gly-Asp(OtBu)-Val-OtBu can be prepared by condensing Z-Asp(OtBu)-OH and H-Val-OtBu to give Z-Asp(OtBu)-Val-OtBu, hydrogenolyzing the latter, coupling the resulting H-Asp(OtBu)-Val-OtBu with Z-Gly-OSu to give Z-Gly-Asp(OtBu)-Val-OtBu and hydrogenolyzing the latter.

The glycine derivatives of formula I, their solvates and their salts inhibit not only the binding of fibrinogen, fibronectin and the Willebrand factor to the fibrinogen receptor of blood platelets (glycoprotein IIb/IIIa), but also the binding of these and further adhesive proteins such as vitronectin, collagen and laminin to the corresponding receptors on the surface of different types of cell. The said compounds therefore influence cell-cell and cell-matrix interactions. In particular, they prevent the formation of blood platelet thrombi and can be used in the control or prevention of illnesses such as thrombosis, stroke, cardiac infarct, inflammation and arteriosclerosis. Further, these compounds have an effect on tumour cells in that they inhibit their metastasis. Accordingly, they can also be used as antitumor agents.

The inhibition of the binding of fibrinogen to the fibrinogen receptor, glycoprotein IIb/IIIa, can be demonstrated as follows:

The glycoprotein IIb/IIIa is obtained-from Triton X-100 extracts of human blood platelets and purified by lectin affinity chromatography (Analytical Biochemistry 151, 1985, 169–177) and chromatography on an Arg-Gly-Asp-Ser affinity column (Science 231, 1986, 1559–62). The thus-obtained receptor protein is bonded to microtitre plates. The specific binding of fibrinogen to the immobilized receptor is determined with the aid of an ELISA system ("enzyme-linked immunosorbent assay"). The IC$_{50}$ values hereinafter correspond to that concentration of the test substance which is required to inhibit the binding of fibrinogen to the immobilized receptor by 50%:

| Product of Example: | 2 | 6 | 7 | 8 | 10 | 11 | 12 | 13 |
|---|---|---|---|---|---|---|---|---|
| IC$_{50}$ (µM) | 0.016 | 0.15 | 0.09 | 0.11 | 0.038 | 0.12 | 0.11 | 0.11 |
| Product of Example: | 14 | 15 | 16 | 17 | 19 | 20 | | |
| IC$_{50}$ (µM) | 0.054 | 0.08 | 0.022 | 0.016 | 0.011 | 0.022 | | |
| Product of Example: | 23 | 24 | 25 | 26 | 27 | | | |
| IC$_{50}$ (µM) | 0.21 | 0.035 | 0.023 | 0.005 | 0.0019 | | | |

The compounds of formula I have a low toxicity. Thus the product of Example 2 has a LD$_{50}$ of 600 mg/kg intravenously in the mouse.

As mentioned earlier, medicaments containing a glycine derivative of formula I, a solvate thereof or a salt thereof are likewise an object of the present invention, as is a process for the manufacture of such medicaments which comprises bringing one or more of the said compounds and, if desired, one or more other therapeutically valuable substances into a galenical administration form. The medicaments can be administered enterally, e.g. orally in the form of tablets, coated tablets, dragees, hard and soft gelatine capsules, solutions, emulsions or suspensions, or rectally, e.g. in the form of suppositories, or as a spray. The administration can, however, also be effected parenterally, e.g. in the form of injection solutions.

The active ingredient can be mixed with pharmaceutically inert, inorganic or organic excipients for the manufacture of tablets, coated tablets, dragees and hard gelatine capsules. Lactose, maize starch or derivatives thereof, talc, stearic acid or its salts can be used e.g. as such excipients for tablets, dragees and hard gelatine capsules. Suitable excipients for soft gelatine capsules are e.g. vegetable oils, waxes, fats and semi-liquid or liquid polyols; depending on the nature of the active ingredient no excipients are, however, generally required in the case of soft gelatine capsules. Suitable excipients for the manufacture of solutions and syrups are e.g. water, polyols, saccharose, invert sugar and glucose, suitable excipients for injection solutions are e.g. water, alcohols, polyols, glycerine and vegetable oils and suitable excipients for suppositories are e.g. natural or hardened oils, waxes, fats and semi-liquid polyols. The pharmaceutical preparations can, moreover, contain preserving agents, solubilizers, stabilizing agents, wetting agents, emulsifying agents, sweetening agents, colouring agents, flavouring agents, salts for varying the osmotic pressure, buffers, coating agents or antioxidants.

For the control or prevention of the illnesses referred to above, the dosage of the active ingredient can vary within wide limits and will, of course, be fitted to the individual requirements in each particular case. In general, in the case of oral or parenteral administration a dosage of about 0.1 to 20 mg/kg, preferably of about 0.5 to 4 mg/kg, per day should be appropriate for adults, although the upper limit just given can also be exceeded when this is shown to be indicated.

EXAMPLE 1

A) A solution of 55 mg of [3-(p-amidinophenyl)-DL-alanyl]-Gly-Asp(OtBu)-Ser(tBu)-OtBu hydroiodide is kept at room temperature for 2 hours under argon in a mixture of 10 ml of methylene chloride and 5 ml of trifluoroacetic acid. After evaporation of the solvent there are obtained 43 mg (86%) of [3-(p-amidinophenyl)-DL-alanyl]-Gly-Asp-Ser-OH trifluoroacetate (2:3), m.p. 223°–224° C. from ethyl acetate/isopropyl ether.

B) The ester starting material is prepared as follows:

a) A solution, cooled to 0° C., of 1.95 g of H-Ser(tBu)-OtBu tosylate in DMF is brought to pH 8 by the addition of N-methylmorpholine. Thereto here is added a solution of 2.1 g of Z-Asp(OtBu)-OSu in 160 ml of DMF. The mixture is stirred at 0° C. under argon for 1 hour and kept in a refrigerator overnight. The residue remaining behind after evaporation of the solvent is taken up in ethyl acetate and washed with saturated sodium bicarbonate solution, water, 10% potassium hydrogen sulphate solution and water, dried, filtered and evaporated. The are obtained 2.09 g (80%) of A-Asp(OtBu)-Ser(tBu)-OtBu, m.p. 79°–80° C. from ethyl acetate/n-hexane.

b) 1.9 g of Z-Asp(OtBu)-Ser(tBu)-OtBu are hydrogenated in 100 ml of methanol in the presence of 0.1 g of Pd/C 10%. After the theoretical amount of hydrogen has been taken up the mixture is filtered and the filtrate is evaporated to dryness. Chromatography on silica gel with methylene chloride/MeOH (98:2) gives 1.28 g (91%) of H-Asp(OtBu)-Ser(tBu)-OtBu, MS: 389 (M+H)$^+$.

c) Analogously as described in a), from Z-Gly-OSu and H-Asp(OtBu)-Ser(tBu)-OtBu there is obtained Z-Gly-Asp(OtBu)-Ser(tBu)-OtBu, yield: 86%, [α]$_D$ –6.9° (c 0.9, MeOH).

d) Analogously as described in b), by hydrogenolyzing Z-Gly-Asp(OtBu)-Ser(tBu)-OtBu there is obtained H-Gly-Asp(OtBu)-Ser(tBu)-OtBu, yield: 75%, MS: 446 (M+H)$^+$.

e) 67 mg of N-methylmorpholine and 250 mg of HBTU are added to a solution of 200 mg of rac N-Z-3-(p-cyanophenyl)alanine (Pharmazie 40, 1985, 305) and 294 mg of H-Gly-Asp(OtBu)-Ser(tBu)-OtBu in 10 ml of DMF under argon and the mixture is held overnight. The oil obtained after evaporation of the solvent is dissolved in ethyl acetate, the solution is washed with 5% sodium bicarbonate solution and water, dried and evaporated. The residue is chromatographed on silica gel with ethyl acetate. There are obtained 160 mg of [N-Z-3-(p-cyanophenyl)-DL-alanyl]-Gly-Asp(OtBu)-Ser(tBu)-OtBu (1:1 mixture of epimers), m.p. 117°–119° C. from ether/n-hexane.

f) A solution of 362 mg of the product of e) in 40 ml of pyridine and 3 ml of triethylamine is stored for 2 days after saturation with H$_2$S, then stirred into water and extracted with ethyl acetate. The product is chromatographed on silica gel with methylene chloride/methanol. There are obtained 270 mg of [N-Z-3-(p-thiocarboxamidophenyl)-DL-alanyl]-Gly-Asp(OtBu)-Ser(tBu)-OtBu (epimer mixture 1:1), MS: 786 (M+H)$^+$.

g) The thioamide of the previous step is dissolved in 30 ml of acetone, treated with 0.6 ml of methyl iodide and heated under reflux for 3 hours. After filtration and concentration the product is precipitated by the addition of ether. There are obtained 181 mg (57%) of [N-Z-3-(p-methylthiocarboximidophenyl)-DL-alanyl]-Gly-Asp(OtBu)-Ser(tBu)-OtBu hydroiodide (epimer mixture 1:1), m.p. 136°–138° C.

h) A solution of 180 mg of the iodide of the previous step in 30 ml of MeOH is treated with 36 mg of ammonium acetate and heated to 60° C. for 5 hours. After cooling and filtration the product is precipitated with ether.

There are obtained 89 mg (51%) of [N-Z-3-(p-amidinophenyl)-DL-alanyl]-Gly-Asp(OtBu)-Ser(tBu)-OtBu hydroiodide (1:1 epimer mixture), m.p. 150° C. (dec.) from ethyl acetate/n-hexane.

i) In an analogous manner to that described under b), by hydrogenolyzing the product of h) there is obtained [3-(p-amidinophenyl)-DL-alanyl]-Gly-Asp(OtBu)-Ser(tBu)-OtBu hydroiodide (1:1 epimer mixture), m.p. 163°–164° C. from ethyl acetate/n-hexane, yield: 70%.

EXAMPLE 2

A) Analogously to that described in Example 1A, by using [N-Boc-3-(p-amidinophenyl)-DL-alanyl]-Gly-Asp(OtBu)-Val-OtBu hydroiodide acetate (1:1) there is obtained [3-(p-amidinophenyl)-DL-alanyl]-Gly-Asp-Val-OH trifluoroacetate (1:2), m.p. 174° (dec.) from methanol/ethyl acetate, yield: 75%.

B) The starting material can be prepared in the following manner:

a) By condensing Z-Asp(OtBu)-OH and H-Val-OtBu there is obtained Z-Asp(OtBu)-Val-OtBu, m.p. 75° C. (n-hexane), yield: 93%.

b) By hydrogenolyzing the product of a) there is obtained H-Asp(OtBu)-Val-OtBu, m.p. 71° (n-hexane), yield: 93%.

c) By coupling Z-Gly-OSu and H-Asp(OtBu)-Val-OtBu there is obtained Z-Gly-Asp(OtBu)-Val-OtBu, m.p.132° C. (ethyl acetate), yield: 87%.

d) By hydrogenolyzing the product of c) there is obtained H-Gly-Asp(OtBu)-Val-OtBu, yield: 87% of theory, [α]$_D$ –33.2° (c 0.6, MeOH).

e) By coupling rac N-Boc-3-(p-cyanophenyl)alanine (French Published Specification 2593 814) and H-Gly-Asp(OtBu)-Val-OtBu there is obtained [N-Boc-3-(p-cyanophenyl)-DL-alanyl]-Gly-Asp(OtBu)-Val-OtBu, m.p. 140°–145° C. from ethyl acetate/isopropyl ether, yield: 66%.

f) Analogously to Example 1 B) f), g), h), from the foregoing compound via [N-Boc-3-(p-thiocarboxamidophenyl)-DL-alanyl]-Gly-Asp(OtBu)-Val-OtBu(epimer mixture 1:1), yield: 96%, MS: 708 (M+H)$^+$, and via [N-Boc-3-(p-methylthiocarboximidophenyl)-DL-alanyl]-Gly-Asp(OtBu)-Val-OtBu hydroiodide (epimer mixture 1:1), m.p 100° C. (dec), yield: 82%, there is obtained [N-Boc-3-(p-amidinophenyl)-DL-alanyl]-Gly-Asp(OtBu)-Val-OtBu hydroiodide acetate (epimer mixture 1:1), m.p. 154°–156° C. (dec.) (ethyl acetate) yield: 89%.

EXAMPLE 3

A) 95 mg of [N-Boc-3-(p-guanidinophenyl)-L-alanyl]-Gly-Asp(OtBu)-Val-OtBu are dissolved in 10 ml of ethyl acetate and treated with 5 ml of 2.5N HCl in ethyl acetate. After stirring at room temperature for 4 hours the mixture is filtered and the precipitate is washed with ethyl acetate. There are obtained 44 mg (53%) of [3-(p-guanidinophenyl)-L-alanyl]-Gly-Asp-Val-OH pentahydrochloride, m.p. 215° C. (dec.) from dioxan.

B) The starting material can be prepared in the following manner:

a) By condensing N-Boc-3-(p-nitrophenyl)-L-alanine and H-Gly-Asp(OtBu)-Val-OtBu there is obtained [N-Boc-3-(p-nitrophenyl)-L-alanyl]-Gly-Asp(OtBu)-Val-OtBu, m.p. 106° C. (n-hexane). Yield: 72%.

b) A solution of 890 mg of the product of a) in 15 ml of methanol is hydrogenated for 3 hours in the presence of 200 mg of 10% Pd/C. The foam remaining behind after filtration and evaporation of the solvent is chromatographed on silica gel with ethyl acetate-methanol (95:5) and crystallized from isopropyl ether. There are obtained 670mg (79%) of [N-Boc-3-(p-aminophenyl)-L-alanyl]-Gly-Asp(OtBu)-Val-OtBu, m.p. 110°–112° C.

c) A solution of 200 mg of the product of b) and 60 mg of 3,5-dimethyl-N-nitro-1H-pyrazole-1-carboxamidine in 3 ml of ethanol is heated under reflux for 24 hours. The solvent is evaporated and the residue is chromatographed on silica gel with methylene chloride/methanol (98:2). After recrystallization from ethyl acetate/n-hexane there are obtained 148 mg (66%) [N-Boc-3-[p-(3-nitroguanidino)phenyl]-L-alanyl-Gly-Asp(OtBu)-Val-OtBu, m.p. 141°–143° C.

d) A solution of 118 mg of the foregoing step in 3 ml of ethyl acetate is hydrogenated for 3 days in the presence of 30 mg of Pd/C. After removal of the solvent the filtrate is chromatographed on silica gel with ethyl acetate/methanol (99:1). There are obtained 59 mg (54%) of [N-Boc-3-(p-guanidinophenyl)-L-alanyl]-Gly-Asp(OtBu)-Val-OtBu, MS: 706 $(M+H)^+$.

EXAMPLE 4

A) Analogously to that described in Example 3A, by the acidic hydrolysis of [N-Boc-3-(p-amidinophenyl)-DL-alanyl]-Gly-Asp(OtBu) isobutylamide hydroiodide there is obtained [3-(p-amidinophenyl)-DL-alanyl]-Gly-Asp isobutylamide hydrochloride (epimer mixture 1:1), m.p. 195°–198° C. (dec.) from dioxan, yield: quantitative.

B) The starting material can be prepared as follows:
a) 5.5 g of isobutylamine dissolved in 5 ml of THF are added dropwise to a mixture, prepared at −10° C., of 5.12 g of Z-Asp(OtBu)-OH hydrate, 1.65 ml of N-methylmorpholine and 2 ml of isobutyl chloroformate in 15 ml of THF. After 3 hours it is freed from solvent, the residue is taken up in ethyl acetate/sodium bicarbonate 5% and the organic phase is washed neutral with water. After drying, evaporation of the solvent and chromatography of the resulting oil on silica gel with ethyl acetate there are obtained 4.53 g (80%) of Z-Asp (OtBu) isobutylamide, m.p. 69°–70° C. from n-hexane.

b) By hydrogenolyzing the product of a) there is obtained H-Asp(OtBu) isobutylamide, yield: 97%, MS: 189, 171.

c) By coupling Z-Gly-OH with the product of b) there is obtained A-Gly-Asp(OtBu) isobutylamide, yield: 87% MS: 436 $(M+H)^+$.

d) By hydrogenolyzing the product of the previous step there is obtained H-Gly-Asp(OtBu) isobutylamide, yield: 42%, MS: 302 $(M+H)^+$.

e) By coupling rac N-Boc-3-(p-cyanophenyl)alanine and rac H-Gly-Asp(OtBu) isobutylamide there is obtained [N-Boc-3-(p-cyanophenyl)-DL-alanyl]-Gly-Asp (OtBu) isobutylamide (1:1 mixture of epimers), m.p. 117°–119° C. (ethyl acetate/n-hexane), yield: 27%.

f) Analogously to Example 1Bf)g)h), via [N-Boc-3-(p-thiocarboxamidophenyl)-DL-alanyl]-Gly-Asp(OtBu) isobutylamide (epimer mixture 1:1) and via [N-Boc-3-(p-methylthiocarboximidophenyl)-DL-alanyl]-Gly-Asp(OtBu) isobutylamide hydroiodide (epimer mixture 1:1), m.p. 145°–147° C. (dec.), yield: 72%, there is obtained [N-Boc-3-(p-amidinophenyl)-DL-alanyl]-Gly-Asp(OtBu) isobutylamide hydroiodide (epimer mixture 1:1), m.p. 175°–178° C., yield: 60%.

EXAMPLE 5

A) Analogously to Example 1 A), by using [N-Z-3-(p-amidinophenyl)-DL-alanyl]-Gly-Asp(OtBu) isobutylamide there is obtained [N-Z-3-(p-amidinophenyl)-DL-alanyl]-Gly-Asp isobutylamide trifluoroacetate (epimer mixture 1:1), m.p. 141°–143° C. (ether), yield: 91%.

B) The starting material can be prepared in the following manner:
a) By coupling rac N-Z-3-(p-cyanophenyl)alanine and H-Gly-Asp(OtBu) isobutylamide there is obtained [N-Z-3-(p-cyanophenyl)-DL-alanyl]-Gly-Asp(OtBu) isobutylamide (epimer mixture 1:1), m.p. 121°–123° C. (ethyl acetate/n-hexane), yield: 91%.

b) Analogously to Example 1B)f)g)h), via [N-Z-3-(p-thiocarboxamidophenyl)-DL-alanyl]-Gly-Asp(OtBu) isobutylamide (epimer mixture 1:1) and via [N-Z-3-(p-methylthiocarboximidophenyl)-DL-alanyl]-Gly-Asp (OtBu) isobutylamide hydroiodide (epimer mixture 1:1) there is obtained [N-Z-3-(p-amidinophenyl)-DL-alanyl]-Gly-Asp (OtBu) isobutylamide hydroiodide (epimer mixture 1:1), m.p. 160°–163° C., yield: 37%.

EXAMPLE 6

A solution of 400 mg of H-Arg-Gly-Asp-Val-OH (Proc. Natl. Acad. Sci. USA, 82, 1985, 8057) and 143 mg of pyridine.HBr in 15 ml of DMF is treated with 435 mg of Z-Aeg(Z)-OSu. The reaction mixture is adjusted to pH 8.5 with N-methylmorpholine, stirred overnight and subsequently evaporated. The residue is dissolved in 0.2N acetic acid and chromatographed on a polysaccharide resin (Sephadex G-10) with 0.2N acetic acid. The uniform fractions are combined and lyophilized. An aqueous solution of the lyophilizate is chromatographed on a polystyrene resin in acetate form (Dowex 44). The eluate is lyophilized. There are obtained 143 mg of Z-Aeg(Z)-Arg-Gly-Asp-Val-OH; MS: 814 $(M+H)^+$.

EXAMPLE 7

A solution of 120 mg of Z-Aeg(Z)-Arg-Gly-Asp-Val-OH (Example 6) in 20 ml of 0.1N acetic acid is hydrogenated in the presence of Pd/C analogously to Example 1Bb). The catalyst is filtered off and the filtrate is lyophilized. There are obtained 72 mg of Aeg-Arg-Gly-Asp-Val-OH.acetate (1:1); MS: 546 $(M+H)^+$.

EXAMPLE 8

A solution of 216 mg of H-Arg- Gly-Asp-Ser-OH (U.S. Pat. No. 4,578,079) in 5 ml of DMF and 5 ml of $H_2O$ is treated with 242 mg of Z-Aeg(Z)-OSu and 0.11 ml of N-methylmorpholine. The reaction mixture is stirred for 18 hours and then adjusted to pH 5.3 with acetic acid. The reaction mixture is extracted with ethyl acetate. The aqueous phase is treated with Pd/C and hydrogenated for 2 hours. The catalyst is filtered off under suction and the filtrate is lyophilized. The lyophilizate is dissolved in 0.2N acetic acid and chromatographed on a polysaccharide resin (Sephadex G 25S) with 0.2N acetic acid. The combined uniform fractions are lyophilized. There are obtained 150 mg of Aeg-Arg-Gly-Asp-Ser-OH-acetate (1:2), MS: 534 $(M+H)^+$.

EXAMPLE 9

A solution of 237.5 mg of H-Arg-Gly-Asp-Val-OH in 5 ml of acetone and 5 ml of $H_2O$ is treated in succession with 226 mg of naphthalene-2-sulphonyl chloride and 168 mg of NaHCO₃. After stirring for 2 hours the mixture is acidified with acetic acid and the acetone is distilled off. The aqueous residue is chromatographed on Sephadex G-25S with 0.2N acetic acid. The combined uniform fractions are lyophilized. There are obtained 172 mg of (2-naphthylsulphonyl)-Arg-Gly-Asp-Val-OH; MS: 636 (M+H)⁺.

EXAMPLE 10

A suspension of 3 g of a carrier consisting of a styrene-1% divinylbenzene resin containing p-benzyloxybenzyl alcohol residues in 30 ml of DMF is treated in succession with 0.6 g of Fmoc-Nal(1)-OH (European Patent Application 128762), 523 mg of HBTU, 16.8 mg of 4-dimethylaminopyridine and 0.24 ml of DIPEA. The reaction mixture is shaken for 24 hours, the resin is subsequently filtered off under suction and washed with DMF. The free hydroxy groups are acetylated for 30 minutes with 1.13 ml of acetic anhydride, 2.05 ml of N-ethyldiisopropylamine in 30 ml of DMF. A synthesis cycle is described in the following protocol:

| Step | Reagent | Time |
| --- | --- | --- |
| 1 | DMF | 2 × 1 min. |
| 2 | 20% piperidine/DMP | 1 × 7 min. |
| 3 | DMF | 5 × 1 min. |
| 4 | 2.5 eq. Fmoc-amino acid/DMF + 2.5 eq. HBTU + 2.5 eq. N-ethyldiisopropylamine | 1 × 90 min. |
| 5 | DMF | 3 × 1 min. |
| 6 | Isopropyl alcohol | 2 × 1 min. |

30 ml of solvent are used in each step. Fmoc-Asp-(OtBu)-OH, Fmoc-Gly-OH, Fmoc-Arg(HCl)-OH are coupled according to the above protocol. Boc-Aeg(Boc)-OSu is introduced into the peptide chain. After completion of the synthesis the peptide resin is dried and divided in half. It is suspended in 10 ml of TFA/5 ml of CH₂Cl₂ and 1 ml of H₂O and shaken for 90 minutes. The resin is filtered off and the filtrate is concentrated. The residue is lyophilized from H₂O. The lyophilizate is chromatographed on a Sephadex G-25S in 0.2N acetic acid. The combined uniform fractions are lyophilized, the lyophilizate is chromatographed on Dowex 44. The eluate is lyophilized. There are obtained 49 mg of N-Aeg-Arg-Gly-Asp-Nal(1)-OH.acetate (1:1), MS: 644 (M+H)⁺.

EXAMPLE 11

Analogously to Example 10, starting from 1.05 g of Fmoc-Ile-OH there are obtained 73.5 mg of Aeg Arg-Gly-Asp-Ile-OH.TFA (1:1), MS: 560 (M+H)⁺.

EXAMPLE 12

A) A solution of 230 mg of Boc-Lys(Z) Gly-Asp(OBzl)-Val-OBzl in 10 ml of methanol is hydrogenated in the presence of Pd/C. The catalyst is filtered off and the filtrate is concentrated. The residue is dissolved in 2 ml of H₂O, adjusted to pH 9.5 with 2N NaOH and treated with 109 mg of methyl acetimidate.HCl. The pH value is again adjusted to 9.5. After stirring for 90 minutes the reaction mixture is acidified to pH 4 with 1N HCl and chomatographed on Sephadex G-25S , with 0.2N acetic acid. The uniform fractions are combined and lyophilized. There are obtained 72 mg of [N2-Boc-N₆-(1-iminoethyl)-L-lysyl]Gly-Asp-Val-OH, MS: 559 (M+H)⁺.

B) The starting material is prepared as follows:

A solution of 583 mg of H-Gly-Asp(OBzl)-Val-OBzl (Example 15Bb) and 477.5 mg of Boc-Lys(Z)-O Su in 10 ml of DMF is adjusted to pH 8.5 with N-methylmorpholine. After stirring for 18 hours the mixture is concentrated and the residue is partitioned between ethyl acetate and water. The organic phase is washed with saturated NaHCO₃ solution, 5% KHSO₄/10% K₂SO₄ solution and saturated NaCl solution, dried and filtered. The filtrate is concentrated and the residue is crystallized from ether. There are obtained 385 mg of Boc-Lys(Z)-Gly-Asp(OBzl)-Val-OBzl, m.p. 95°–101° C.

EXAMPLE 13

A) 370 mg of o-[Z-Arg(Z₂)-Gly-Asp(OtBu)-NH]-benzoic acid are dissolved in 50 ml of methanol and hydrogenated in the presence of Pd/C. The filtrate from the catalyst is concentrated in a vacuum, the residue is dissolved in 50 ml of DMF and treated with 46 mg of pyridine.HCl and 0.07 ml of DIPEA. 203 mg of HOBTU are placed in 100 ml of DMF and the above solution is added dropwise under argon. After stirring for 20 hours a further 101.5 mg of HOBTU and 0.035 ml of DIPEA are added thereto. The reaction mixture is stirred for 18 hours and concentrated. The residue is dissolved in methanol/water and chromatographed on Dowex 44. The eluate is concentrated, the residual is dissolve in 20 ml of TFA and concentrated after 30 minutes. After chromatography on a chemically-modified silica gel (Lichrosorb RP18) with 0.1% TFA-ethanol there are obtained 102 mg of N-[(o-azidobenzoyl)-Arg-Gly-Asp]-anthranilic acid trifluoroacetate (1:1), MS: 611 (M+H)⁺.

The acid starting material is prepared as follows:

A solution of 1.6 g of Z-Asp(OtBu)-OH and 2 g of benzyl anthranilate tosylate in 10 ml of DMF is treated with 1.92 g of TOBTU and 1.78 ml of DIPEA. After stirring for 20 hours the reaction mixture is partitioned between ethyl acetate and water. The organic phase is washed with 5% KHSO₄/10% K₂SO₄ solution, water, saturated NaHCO₃ solution, water and saturated NaCl solution and dried over Na₂SO₄. The drying agent is filtered off and the filtrate is concentrated. After crystallization from ethanol there is obtained 0.75 g of N-[Z-Asp(OtBu)]-anthranilic acid, m.p. 123°–124° C.

b) Analogously to Example 7, by hydrogenating the product of a) there are obtained 401 mg of N-[H-Asp(OtBu)]-anthranilic acid.

c) A suspension of 401 mg of the product of b) in 10 ml of DMF is treated with 612 mg of Z-Gly-OSu. The reaction mixture is adjusted to pH 8.5 with N-methylmorpholine and stirred for 4 hours. The reaction solution is treated with 0.52 ml of diethylaminoethylamine, stirred for 10 minutes and then partitioned between ethyl acetate and 5% KHSO₄/10% K₂SO₄ solution. The organic phase is washed with saturated sodium chloride solution and dried. After filtration the filtrate is concentrated. The residue is dissolved in methanol and hydrogenated in the presence of Pd/C. The catalyst is filtered off and the filtrate is concentrated. The residue is dissolved in 10 ml of DMF, treated with 673 mg of Z-Arg(Z₂)-OSu and adjusted to pH 8.5 with N-methylmorpholine. After stirring for 18 hours the product is precipitated by pouring into 5% KHSO₄/10% K₂SO₄ solution. By chromatography on silica gel with methylene chloride/methanol there are obtained, after recrystallization from ethanol, 410 mg of o-[Z-Arg(Z₂)-Gly-Asp(OtBu)-NH]-benzoic acid, m.p. 102°–103° C.

EXAMPLE 14

A) A solution of 109 mg of Boc-Arg-Gly-Asp-Val-OH in 3 ml of 0.2M sodium borate buffer (pH 9) is treated with 55.5 mg of 1,2-cyclohexanedione and then stirred under argon for 24 hours. The reaction solution is acidified to pH 4 with acetic acid and chromatographed on Sephadex G-25S with 0.2N acetic acid. The uniform fractions are combined and lyophilized. There are obtained 46 mg of [N2-Boc-N5-(3a,4,5,6,7,7a-hexahydro-3a,7a-dihydroxy-1H-benzimidazol-2-yl)-L-ornithyl]-Gly-Asp-Val-OH, MS: 658 $(M+H)^+$.

B) For the preparation of the acid starting material, a solution of 1 g of H-Arg-Gly-Asp-Val-OH and 340 mg of pyridine.HBr in 15 ml of dioxan and 15 ml of $H_2O$ is treated in succession with 480 mg of di-t-butyl dicarbonate and 0.59 g of $NaHCO_3$. After stirring for 18 hours the reaction mixture is concentrated. The residue is purified on a porous styrene-divinylbenzene copolymer resin (MCI gel CHP2OP) with water/ethanol. The combined uniform fractions are concentrated and lyophilized from water. There are obtained 260 mg of Boc-Arg-Gly-Asp-Val- —OH, MS: 546 $(M+H)^+$.

EXAMPLE 15

A) A solution of 275.5 mg of N-Boc-3-(p-aminophenyl)-DL-alanyl-Gly-Asp-Val-OH in 3 ml of water is treated in succession with 138 mg of $K_2CO_3$ and 124 mg of aminoiminomethanesulphonic acid. After stirring for 18 hours the reaction mixture, is acidified with glacial acetic acid and chromatographed on Sephadex G-25S with 0.2N acetic acid. The uniform fractions are combined and lyophilized. There are obtained, 205 mg of Boc [N-Boc-3-(p-guanidinophenyl)-DL-alanyl]-Gly-Asp-Val-OH potassium salt (1:1), MS: 632 $(M+H)^+$.

B) The starting material is prepared as follows:

a) A solution, cooled to −20° C., of 32.3 g of Boc-Asp-(OBzl)-OH in 150 ml of DMF is treated with 11 ml of N-methylmorpholine and 13.07 ml of isobutyl chloroformate. The suspension obtained is stirred at −15° C. and treated with a suspension, cooled to −20° C., of 37.95 g of H-Val-OBzl.tosylate and 11 ml of N-methylmorpholine in 150 ml of DMF. The reaction mixture is stirred at below −10° C. for 10 minutes and at room temperature for 2 hours, filtered and the filtrate is concentrated. The residue is dissolved in ethyl acetate and washed with 5% $KHSO_4$/10% $K_2SO_4$ solution, water, saturated $NaHCO_3$ solution, water and saturated NaCl solution and dried. The organic phase is concentrated. 52.9 g of Boc-Asp(OBzl)-Val-OBzl are obtained. 10.24 g thereof are dissolved in 30 ml of TFA and then concentrated. The residue, is crystallized from ethyl acetate/hexane. There are obtained 8.3 g of H-Asp- (OBzl)-Val-OBzl.TFA (1:1),.m.p. 147°–148° C.

b) A solution of 4.2 g. of H-Asp(OBzl)-Val-OBzl.TFA in 50 ml of ethyl acetate is treated in succession with 2.72 g of Boc-Gly-OSu and 0.88 ml of N-methylmorpholine and then stirred at 20° C. for 72 hours. The reaction mixture is partitioned between ethyl acetate and water and the organic phase is washed with 5% $KHSO_4$/10% $K_2SO_4$ solution, water, saturated $NaHCO_3$ solution, water and saturated NaCl solution. After drying the solution is concentrated. The residue is dissolved in 30 ml of trifluoroacetic acid held at 20° C. for 20 minutes and then concentrated. After crystallization from ethyl acetate/hexane there are obtained 3.5 g of H-Gly-Asp (OBzl)-Val-OBzl, TFA (1:1), m.p. 150°–151° C.

c) A solution of 1.08 g of rac N-Boc-3-(4nitrophenyl)-alanine and 2.04 g of H-Gly-Asp(OBzl)-Val-OBzl.TFA in 15 ml of DMF is treated in succession with 1.4 g of HBTU and 1.23 ml of N-ethyldiisopropylamine. After stirring for 3 hours the reaction mixture is partitioned between ethyl acetate and water. The batch is worked-up as described under b) and, after crystallization from ethyl acetate/hexane, there are obtained 1.8 g of N-Boc-3-(4-nitrophenyl)-DL-alanyl-Gly-Asp(OBzl)-Val-OBzl, m.p. 155°–157° C.

d) A solution of 1.5 g of N-Boc-3-(4-nitrophenyl)-DL-alanyl-Gly-Asp(OBzl)-Val-OBzl in 50 ml of 90% glacial acetic acid is hydrogenated in the presence of 10% Pd/C. The filtrate from the catalyst is lyophilized from water. There are obtained 910 mg of N-Boc-3-(4-aminophenyl)-DL-alanyl-Gly-Asp-Val-OH, MS: 552 $(M+H)^+$.

EXAMPLE 16

A) Analogously to Example 1A), by the acidolysis of [N-Boc-3-(p-amidinophenyl)-DL-alanyl]-Gly-Asp(OtBu)-Nal(1)-OH there is obtained [3-(p-amidinophenyl)-DL-alanyl]-Gly-Asp-Nal(1)-OH.TFA (1:2) (1:1 epimer mixture), m.p. 170° C. (dec.) (ethanol/ethyl acetate).

B) The starting material is prepared in the following manner:

a) Analogously to Example 1 B)a), by coupling Z-Gly-OH and H-Asp(OtBu)-OMe there is obtained Z-Gly-Asp(OtBu)-OMe, m.p. 92°–95° C.(hexane), yield: 89% of theory.

b) 70 ml of 1N NaOH are added dropwise while cooling to a solution of 27.0 g of the product of the previous step in 200 ml of acetone and the stirring is continued for 2 hours. The pH is adjusted to 4 by the addition of 10% aqueous citric acid and the solvent is evaporated, whereby the crude product separates. After recrystallization from ether/hexane there are obtained 19.04 g of Z-Gly-Asp-(OtBu)-OH, m.p. 101°–104° C., yield: 70%.

c) Analogously to Example 1 B)a), by coupling the product of the previous step with H-Nal(1)-OMe there is obtained Z-Gly-Asp(OtBu)-Nal(1)-OMe, m.p. 59° C. (hexane), yield: 34%.

d) Analogously to Example 1 B)b), by hydrogenolyzing the product of the previous step there is obtained H-Gly-Asp-(OtBu)-Nal(1)-OMe, m.p. 67°–68° C. (hexane), yield: 72%.

e) Analogously to Example 1 B)e), by coupling N-Boc-3-(p-cyanophenyl)-DL-alanine with the product of the previous step there is obtained [N-Boc-3-(p-cyanophenyl)-DL-alanyl]-Gly-Asp(OtBu)-Nal(1)-OMe (epimers), yield: quantitative, MS: 730 $(M+H)^+$.

f) Analogously to Example 1 B)f), by thionylating the product of the previous step there is obtained [N-Boc-3-[p-(thiocarbamoyl)phenyl]-DL-alanyl]-Gly-Asp (OtBu)-Nal(1)-OMe (epimers), m.p. 110°–112° C., yield 75%.

g) Analogously to Example 1 B)g), by methylating the product of the previous step there is obtained [N-Boc-3-[p-[(methylthio)formimidoyl]phenyl]-DL-alanyl]-Gly-Asp(OtBu)-Nal(1)-OMe hydroiodide (epimers), m.p. 128°–130° C. (ether), yield: 64%.

h) Analogously to Example 1 B)h) by reacting the product of the previous step with $NH_4OAc$ there is obtained [N-Boc-3(p-amidinophenyl)-DL-alanyl]-Gly-Asp (OtBu)-Nal(1)-OMe hydroiodide (epimers), m.p. 139°–141° C. (ether), yield\70%.

i) As described in paragraph b), from the product of the previous step there is obtained [N-Boc-3-(p-amidinophenyl)-DL-alanyl]-Gly-Asp(OtBu)-Nal(1)-OH (epimers), m.p. 206° C. (ethyl acetate), yield: 97%.

EXAMPLE 17

30 mg of triethylamine and 24 mg of di-t-butyl dicarbonate are added at room temperature while gassing with argon to a solution of 70 mg of [3-(p-amidinophenyl)-DL-alanyl]-Gly-Asp-Val-OH trifluoroacetate (1:2) (1:1 mixture of epimers) (Example 2) in 0.6 ml of DMF and the mixture is stirred for 75 minutes. After the addition of acetic acid to pH 4 the mixture is evaporated to dryness and the residue is crystallized with ethyl acetate. After recrystallization from methanol/ethyl acetate there is obtained [N-Boc-3-(p-amidinophenyl)-DL-alanyl]-Gly-Asp-Val-OH (1:1 epimers), yield: 63%.

EXAMPLE 18

A) Analogously to Example 1A, by using [N-Boc-3-(p-amidinophenyl)-DL-alanyl]-Gly-Asp(OtBu) p-fluorophenethylamide hydroiodide (1:1 epimers) there is obtained 3-(p-amidinophenyl)-DL-alanyl-Gly Asp p-fluorophenethylamide trifluoroacetate (5:8) (epimers), m.p. 192°–195° C. (ethanol/ethyl acetate), yield: 61%.

B) The ester starting material is prepared as follows:
a) Analogously to Example 1 B)e), by coupling Z-Gly-Asp(OtBu)-OH (Example 16 B)b)) and 4-fluorophenethylamine with HBTU there is obtained Z-Gly-Asp(OtBu) p-fluorophenethylamide, MS: 502 (M+H)⁺.
b) Analogously to Example 1 B)b), by catalytically hydrogenolyzing the product of the previous step there is obtained H-Gly-Asp(OtBu) p-fluorophenethylamide, MS: 368 (M+H)⁺.
c) Analogously to Example 1B)e), by coupling rac N-Boc- 3-(p-cyanophenyl)alanine with the product of the previous step there is obtained [N-Boc-3-(p-cyanophenyl)-DL-alanyl]-Gly-Asp(OtBu) p-fluorophenethylamide (1:1 epimers), MS: 662 (M+Na⁺).
d) Analogously to Example 1 B)f), by reacting the product of the previous step with H₂S there is obtained [N-Boc-3-[p-(thiocarbamoyl)phenyl]-DL-alanyl]-Gly-Asp (OtBu) p-fluoro- phenethylamide (1:1 epimers), MS: 674 (M+H)⁺.
e) Analogously to Example 1 B)g), by reacting the product of the previous step with MeI there is obtained [N-Boc-3-[p-(methylthioformimidoyl)phenyl]-DL-alanyl]-Gly-Asp-(OtBu) p-fluorophenethylamide hydroiodide (1:1 epimers), m.p. 134°–136° C. (dec.) (ether).
f) Analogously to Example 1 B)h), by reacting the product of the previous step with ammonium acetate there is obtained [N-Boc-3(p-amidinophenyl)-DL-alanyl]Gly-Asp-(OtBu) p-fluorophenethylamide hydroiodide (1:1 epimers), m.p. 90°–92° C. (dec.) from ether.

EXAMPLE 19

A) Analogous to Example 1A), by using (p-amidinohydrocinnamoyl)-Gly-Asp(OtBu)-Nal(1)-OH- there is obtained (p-amidinohydrocinnamoyl)-Gly Asp-Nal (1)-OH trifluoroacetate (1:1), m.p. 196°–199° C. (ethanol/ether), yield: 48%.

B) The ester starting material is prepared as follows:
a) Analogously to Example 1 B)e), by coupling 3-(p-cyanophenyl)propionic acid and H-Gly-Asp(OtBu)-Nal(1)-OMe (Example 16 B)d) ) there is obtained (p-cyanohydrocinnamoyl)-Gly-Asp(OtBu)-Nal(1)-OMe, m.p. 112°–113° C. (CH₂Cl₂/hexane).
b) Analogously to Example 1 B)f)g)h), by reacting the product of the previous step in succession with H₂S, MeI and ammoniumacetate there is obtained (p-amidinohydrocinnamoyl)-Gly-Asp(OtBu)-Nal(1)-OMe hydroiodide, m.p. 140°–142° C. (ether).
c) Analogously to Example 16 B)b), by the alkaline saponification of the product of the previous step there is obtained (p-amidinohydrocinnamoyl)-Gly-Asp(OtBu)-Nal(1)-OH, m.p. 236°–237° C. (water).

EXAMPLE 20

Analogously to Example 1A), by using [N-Boc-3-(p-amidinophenyl)-D-alanyl]-Gly-Asp(OtBu)-Val-OtBu hydroiodide there is obtained [3-(p-amidinophenyl)-D-alanyl]-Gly-Asp-Val-OH trifluoroacetate (1:2), m.p. 128° C. (dec.) (ether), yield: quantitative

EXAMPLE 21

A) Analogously to Example 16 B)b), by saponifying methyl [N-[[N-Boc-3-(p-amidinophenyl)-DL-alanyl]-Gly-Asp(OtBu)]-p-amino]benzoate hydroiodide (epimers 1:1) there is obtained [N-[[N-Boc-3-(p-amidinophenyl)-DL-alanyl]-Gly-Asp]p-amino]benzoic acid (1:1 epimers), m.p. 205°–206° C. (methanol), yield: 48%.

B) The starting material is prepared in the following manner:
a) Analogously to Example 1 B)a), by coupling Z-Gly-Asp(OtBu)-OH and benzyl p-aminobenzoate there is obtained benzyl [N-[Z-Gly-Asp(OtBu)]-p-amino] benzoate, yield: 32%, MS: 590 (M+H)⁺.
b) Analogously to Example 1 B)b), by hydrogenolyzing the product of the previous step there is obtained [N-[Gly-Asp(OtBu)]-p-amino]benzoic acid, m.p. 160° C. (dec.) from methanol/AcOEt.
c) From the product of the previous step by methylation with diazomethane there is obtained methyl [N-[Gly-Asp-(OtBu)]-p-amino]benzoate, m.p. 78°–82° C. (hexane), yield: 77%.
d) Analogously to Example 1 B)e), by coupling rac N-Boc-3-(4-cyanophenyl)alanine and the product of the previous step there is obtained methyl [N-[[N-Boc-3-(p-cyanophenyl)-DL-alanyl]-Gly-Asp(OtBu)]-p-amino]benzoate (1:1 mixture of epimers), m.p. 108° C. (ethyl acetate/hexane), yield: 51%.
e) Analogously to Example 1 B)f)g), from the product of the previous step by thionylation and methylation there is obtained methyl [N-[[N-Boc-3-[p-(methylthioformimidoyl)-phenyl]-DL-alanyl]-Gly-Asp(OtBu)]-p-amino]benzoate hydroiodide (epimers 1:1), m.p. 150°–151° C.(ether), yield: 77%.
f) Analogously to Example 1 B)h), from the product of the previous step by ammonolysis there is obtained methyl [N-[[N-Boc-3-(p-amidinophenyl)-DL-alanyl]-Gly-Asp(OtBu)]-p-amino]benzoate hydroiodide (epimers 1:1), m.p. 179°–181° C. (dec.) (ether), yield: 79%.

EXAMPLE 22

Analogously to Example 1A), by hydrolyzing the product of Example 21 there is obtained [N [[3-(p-amidinophenyl)

-DL-alanyl]-Gly-Asp]-p-amino]benzoic acid (epimers 1:1), m.p. 214°–216° C. (MeOH), yield: 78%.

EXAMPLE 23

A) A solution of 180 mg of (p-cyanohydrocinnamoyl)-Gly-Asp-Val-OH in a mixture of 10 ml of methanol/conc. aqueous ammonia solution (2:1) is hydrogenated in the presence of 180 mg of Raney-nickel. After 20 hours the catalyst is filtered off and the filtrate is evaporated to dryness. The residue is purified on anion exchange resin in H$^+$ form and crystallized with hexane. There is obtained (p-aminomethylhydrocinnamoyl)-Gly-Asp-Val-OH, m.p. 175° C. (dec.), yield: 25%.

B) The nitrile starting material, m.p. 132°–134° C. (ethyl acetate/hexane), is prepared (yield 69%) in analogy to Example 1A) by acidolysis of (p-cyanohydrocinnamoyl)-Gly-Asp(OtBu)-Val-OtBu (Example 24 B)a).

EXAMPLE 24

A) Analogously to Example 19A), from (p-amidinohydrocinnamoyl)-Gly-Asp(OtBu)-Val-OtBu hydroiodide there is obtained (p-amidinohydrocinnamoyl)-Gly-Asp-Val-OH.trifluoroacetate (1:1.1), m.p. 141°–143° C. (ether), yield: quantitative.

B) The ester starting material is prepared as follows:

a) Analogously to Example 1 B)e), by coupling p-cyanohydrocinnamic acid with. H-Gly-Asp(OtBu)-Val-OtBu (Example 2 B)d)) there is obtained (p-cyanohydrocinnamoyl)-Gly-Asp(OtBu)-Val-OtBu, m.p. 132°–134° C. (AcOEt/hexane), yield; 87%.

b) Analogously to Example 1Bf), by thionylating the product of the previous step there is obtained p-(thiocarbamoyl)hydrocinnamoyl-Gly-Asp(OtBu)-Val-OtBu, m.p. 70°–73° C. (hexane), yield: 72%.

c) Analogously to Example 1Bg), by methylating the product of the previous step there is obtained p-[(methylthio)formimidoyl]hydrocinnamoyl-Gly-Asp(OtBu)-Val-OtBu hydroiodide, m.p. 55°–60° C. (ether/hexane), yield: 94%.

d) Analogously to Example 1Bh), by ammonolyzing the product of the previous step there is obtained (p-amidinohydrocinnamoyl)-Gly-Asp(OtBu)-Val-OtBu hydroiodide, m.p. 116°–120° C. (hexane), yield: 90%.

EXAMPLE 25

Analogously to Example 1A), from [N-Boc-3-(p-amidinophenyl)-L-alanyl]-Gly-Asp(OtBu)-Val-OtBu hydroiodide there is obtained [3-(p-amidinophenyl)-L-alanyl]-Gly-Asp-Val-OH trifluoroacetate (2:3), m.p. 164°–166° C. (EtOH/AcOEt), yield: 75%.

EXAMPLE 26

A) Analogously to Example 1A), by the acidolysis of [(p-amidinophenoxy)acetyl]-Gly-Asp(OtBu)-Val-OtBu hydroiodide with TFA there is obtained (p-amidinophenoxy) acetyl-Gly-Asp Val-OH trifluoroacetate,. m.p. 140° C. (ethyl acetate/hexane), yield: 67%

B) The ester starting material can be prepared as follows:

a) Analogously to Example 1 B)e), by coupling p-cyanophenoxyacetic acid and H-Gly-Asp(OtBu)-Val-OtBu there is obtained [p-(cyanophenoxy)acetyl] Gly-Asp(OtBu)-Val-OtBu, m.p. 55° C. (ethyl acetate/hexane), yield: 81% .

b) Analogously to Example 1 B)f), by reacting the product of the previous step with H$_2$S there is obtained [p-(thiocarbamoyl)phenoxyacetyl]-Gly-Asp(OtBu)-Val-OtBu, yield: 80% of theory, MS: 595 (M+H)$^+$.

c) Analogously to Example 1 B)g), by reacting the product of the previous step with methyl iodide there is obtained p-[(methylthio)formimidoyl]phenoxyacetyl-Gly-Asp(OtBu)-Val-OtBu hydroiodide, yield: 83%, MS: 609 (M+H)$^+$.

d) Analogously to Example 1 B)h), by reacting the product of the previous step with ammonium acetate there is obtained [(p-amidinophenoxy)acetyl]-Gly-Asp(OtBu)-Val-OtBu hydroiodide, m.p. 102°–106° C. (ethyl acetate/hexane), yield: 83%.

EXAMPLE 27

A) Analogously to Example 1A ), by using (p-amidinophenyl)acetyl-Gly-Asp(OtBu)-Val-OtBu hydroiodide there is obtained (p-amidinophenyl)acetyl-Gly-Asp-Val-OH trifluoroacetate (5:4), m.p. 175°–178° C. (acetonitrile/methanol), yield 53%.

a) Analogously to Example 1 B)e), by coupling p-cyanophenylacetic acid (J. Chem. Soc. 1941, 744) and H-Gly-Asp(OtBu)-Val-OtBu (Example 2 B)d)) there is obtained (p-cyanophenyl)acetyl-Gly-Asp (OtBu)-Val-OtBu, m.p. 111° C. (ethyl acetate/hexane), b) Analogously to Example 1 B)f)g)h), by reacting the product of the previous step with H$_2$S, MeI and ammonium acetate there is obtained (p-amidinophenyl) acetyl-Gly-Asp(OtBu)-Val-OtBu, MS: 562 (M+H)$^+$.

EXAMPLE 28

A) 216 mg of N-[N-[N-(benzyloxycarbonyl)-3-[p-[N-(benzyloxycarbonyl)amidino]phenyl]-DL-alanyl]glycyl]β-alanine benzyl ester and 72 mg of 5% Pd/C in 4.3 ml of ethanol/acetic acid (19:1) are stirred under hydrogen for 28 hours. The product is chromatographed on silica gel with methanol/acetic acid (9:1). The pure fractions are evaporated, the residue is dissolved in dilute hydrochloric acid, filtered, neutralized with dilute ammonia, filtered and the filtrate is evaporated. The residue is taken up in methanol, filtered and the filtrate is treated with ether. The precipitation is removed by centrifugation, washed with ether and dried. There are obtained 28 mg of N-[N-[3-(p-amidinophenyl)-DL-alanyl]glycyl]-β-alanine dihydrochloride, MS: 336(27, M+H).

B) For the preparation of the ester starting material, N-(benzyloxycarbonyl)-3-(p-cyanophenyl)-DL-alanine and N-glycyl-β-alanine benzyl ester trifluoroacetate are coupled to give N-[N-[N-(benzyloxycarbonyl)-3-(p-cyanophenyl)-DL-alanyl]glycyl]-β-alanine benzyl ester, m.p. 134°–135° C. Therefrom with hydrogen sulphide and triethylamine in pyridine there is obtained N-[N-[N-(benzyloxycarbonyl)-3-[p-(thiocarbamoyl)phenyl]-DL-alanyl]glycyl]-β-alanine benzyl ester m.p.150°–151° C. Reaction with methyl iodide in acetone, subsequent reaction with ammonium acetate in methanol and treatment with benzyl chloroformate and triethylamine in THF give N-[N-[N-(benzyloxycarbonyl)-3-[p-[N-(benzyloxycarbonyl)-amidino]phenyl]-DL-alanyl] glycyl]-β-alanine benzyl ester, MS: 694 (100, M+H).

EXAMPLE 29

From 178 mg of N-[N-[N-[(p-amidinophenoxy)acetyl] glycyl-3-t-butoxy-L-alanyl]-3-phenyl-L-alanine t-butyl ester hydroiodide there are obtained, after treatment with trifluoroacetic acid in methylene chloride as described in Example 1, 91 mg of the trifluoroacetate of N-[N-[N-[(p-amidinophenoxy)acetyl]glycyl]-L-α-aspartyl]-3-phenyl-L-alanine, m.p. 175°–179° C.

The starting material can be prepared as follows:

a) By coupling 7.0 g of Z-Asp(OtBu)-O-Su with 4.72 g of Phe-O-tBu.HCl in the manner described in Example 1B)a) there are isolated, after working-up, chromatography on silica gel (ethyl acetate) and recrystallization, 7.1 g of N-[N-[(benzyloxy)carbonyl]-3-(t-butoxycarbonyl)-L-alanyl]-3-phenyl-L-alanine t-butyl ester m.p. 94°–95° C.

b) After catalytically hydrogenating the product of the previous step in ethanol in the presence of 10% Pd/C at room temperature and under normal pressure there are obtained, after chromatography on silica gel with ethyl acetate, 5.94 g of H-Asp(OtBu)-Phe-O-tBu, $[\alpha]_D$=+9.16° (c=0.6, $CH_3OH$).

c) As set forth in Example 1B)a), from the reaction of 4 g of H-Asp(OtBu)-Phe-O-tBu with 3.43 g of Z-Gly-OSu there are obtained, after chromatography on silica gel with ethyl acetate, 3.9g of N-[N-[N-[(benzyloxy)carbonyl]glycyl]-3-(t-butoxycarbonyl)-L-α-aspartyl]-3-phenyl-L-alanine t-butyl ester.

d) In analogy to Example 1, by hydrogenolyzing the product of the previous step (2.19 g) there are obtained, after chromatography ($CH_2Cl_2/CH_3OH$ 9:1) and recrystallization, 909 mg of N-[N-glycyl-3-(t-butoxycarbonyl)-L-α-aspartyl]-3-phenyl-L-alanine t-butyl ester, m.p. 99°–100° C.

e) Analogously to Example 1B)e), by coupling 675 mg of the product of the previous step with 266 mg of p-cyanophenoxyacetic acid there are obtained, after chromatography on silica gel (ethyl acetate) and recrystallization, 687 mg of N-[3-(t-butoxycarbonyl)-N-[N-[(p-cyanophenoxy)acetyl]glycyl]-L-alanyl]-3-phenyl-L-alanine t-butyl ester, m.p. 83°–85° C. (ethyl acetate/hexane).

f) Analogously to Example 1B)f), after reacting the product of the previous step (650 g) with $H_2S$ there are isolated, after chromatography (ethyl acetate) and crystallization, 405 mg of N-[3-(t-butoxycarbonyl)-N-[N-[[(p-thiocarbamoyl)phenoxy]acetyl]glycyl]-L-alanyl]-3-phenyl-L-alanine t-butyl ester, m.p. 83°–86° C. (hexane).

g) from 390 mg of the product of the previous step there are obtained, after methylation in accordance with Example 1B)g), 375 mg of N-[3-(t-butoxycarbonyl)-N-[N-[[[p-(1-(methylthio)formimidoyl]phenoxy]acetyl]glycyl]-L-alanyl]-3-phenyl-L-alanine t-butyl ester hydroiodide, m.p. 162° C. (ethyl acetate/methanol).

h) Reaction of 358 mg of the material from the previous step with ammonium acetate analogously to Example 1B) h) yields 267 mg of N-[N-[N-[(p-amidinophenoxy)acetyl]-glycyl]-3-t-butoxy-L-alanyl]-3-phenyl-L-alanine t-butyl ester hydroiodide, decomposition point 76° C. (ethyl acetate/hexane).

EXAMPLE 30

Treatment of 140 mg of N-[N-[N-[[2-(p-amidinophenyl)-1,3-dioxolan-2-yl]acetyl]glycyl]-3-(t-butoxycarbonyl)-L-alanyl]-3-phenyl-L-alanine t-butyl ester hydroiodide with trifluoroacetic acid in methylene chloride gives 158 mg of N-[N-[N-[[2-(p-amidinophenyl)-1,3-dioxolan-2-yl]acetyl] glycyl]-L-α-aspartyl]-3-phenyl-L-alanine trifluoroacetate (1:1). A portion of this material is purified by chromatography (RP-18; elution with water, then water/acetonitrile 2:1) and recrystallization, whereby there is obtained a product with m.p. 242°–245° C.

The starting material can be prepared as follows:

a) A mixture of 8 g of ethyl 4-cyanobenzoyl acetate, 80 ml of ethylene glycol, 0.3 g of p-toluenesulphonic acid and 250 ml of toluene is boiled on a water separator. After completion of the reaction the solvent is removed and the residue is partitioned in methylene chloride/0.1N sodium hydroxide solution. The organic extracts are dried, filtered and concentrated. After chromatography (silica gel; hexane/ethyl acetate 1:1) there are obtained 4.4g of a colourless oil which is dissolved in 30 ml of ethanol. 15 ml of 1N sodium hydroxide solution are added dropwise thereto while cooling with an ice bath and the mixture is subsequently left to stand at room temperature for 6 hours. After removing the ethanol the aqueous phase is extracted with ethyl acetate and neutralized with 1N hydrochloric acid. The separated crystals are filtered off, washed with water and dried. There are obtained 2.3 g of 4-cyanobenzoylacetic acid ethylene ketal, m.p. 151°–152° C.

b) Analogously to Example 1B)e), by coupling 256 mg of 4-cyanobenzoylacetic acid ethylene ketal and 449 mg of H-Gly-Asp(OtBu)-Phe-OtBu (Example 29d) there are obtained, after chromatography and recrystallization, 390 mg of N-[3-(t-butoxycarbonyl)-N-[N-[[2-(p-cyanophenyl)-1,3-dioxolan-2-yl]acetyl] glycyl]-L-alanyl]-3-phenyl-L-alanine t-butyl ester, m.p. 81°–82° C. (hexane).

c) The product of the previous step (360 mg) is reacted with $H_2S$ as described in Example 1B)f) to give 323 mg of N-[3-(t-butoxycarbonyl)-N-[N-[[2-[p-(thiocarbamoyl)phenyl]-1,3-dioxolan-2-yl]acetyl] glycyl]-L-alanyl]-3-phenyl-L-alanine t-butyl ester, m.p. 96°–98° C. (hexane).

d) Methylation of 280 mg of the product of the previous step is carried out as in Example 1B)g) and yields 324 mg of N-[3-(t-butoxycarbonyl)-N-[N-[[2-[p-[1-(methylthio)formimidoyl]phenyl]-1,3-dioxolan-2-yl] acetyl]glycyl]-L-alanyl]-3-phenyl-L-alanine t-butyl ester hydroiodide (1:1), m.p. 110°–112° C. (acetone/diethyl ether).

e) Ammonolysis of 250 mg of the product of the previous step analogously to Example 1B)h) gives 200 mg of N-[N-[N-[[2-(p-amidinophenyl)-1,3-dioxolan-2-yl] acetyl]glycyl]-3-(t-butoxycarbonyl)-L-alanyl]-3-phenyl-L-alanine t-butyl ester hydroiodide (1:1), m.p. 129°–130° C.

EXAMPLE 31

A solution of 100 mg of N-[N-[N-[[2-(p-amidinophenyl)-1,3-dioxolan-2-yl]acetyl]glycyl]-L-α-aspartyl]-3-phenyl-L-alanine trifluoroacetate in 10 ml of trifluoroacetic acid/water 9:1 is left to stand at room temperature overnight. After removal of the solvent, chromatography of the residue (RP-18; elution with water-water/acetonitrile 1:1) and recrystallization there are obtained 33 mg of N-[N-[N-[(p-amidinobenzoyl)acetyl]glycyl]-L-aspartyl]-3-phenyl-L-alanine trifluoroacetate (1:1), m.p. 225°–230° C. (decomposition).

EXAMPLE 32

From 50 mg of N-[N-[N-[3-(1-amidino 4-piperidinyl) propionyl]glycyl]-3-t-butoxycarbonyl)-L-alanyl]-3-phenyl- L-alanine t-butyl ester there are obtained in analogy to Example 1A), after recrystallization, 32 mg of N-[N-[N-[3-(1-amidino-4-piperidinyl)propionyl]glycyl]-L-α-aspartyl]-3-phenyl-L-alanine trifluoroacetate (1:1), m.p. 146°–148° C. (ether; decomposition).

The starting material can be prepared as follows:

a) 500 mg of 4-piperidinepropionic acid are added at 2° C. to a solution of 553 mg of S-methyl-isothiourea sulphate in 3.2 ml of 2N sodium hydroxide solution. After leaving to stand at room temperature overnight the separated crystals are filtered off, washed with water, acetone and ether and dried. There are obtained 600 mg of 1-amidino-4-piperidinepropionic acid, m.p. above 275° C.

b) Analogously to Example 1B)e), by coupling 1.6 g of 1-amidino-4-piperidinepropionic acid with 1.8 g of H-Gly-Asp(OtBu)-Phe-OtBu in the presence of 928 mg of pyridinium hydrochloride there are obtained 2.1 g of N-[N-[N-[3-(1-amidino-4-piperidinyl)propionyl] glycyl]-3-t-butoxycarbonyl)-L-alanyl]-3-phenyl-L-alanine t-butyl ester, m.p. 104°–106° C. (diisopropyl ether; decomposition).

EXAMPLE 33

In analogy to Example 1A), from 17 mg of 1-[[N-[N-(p-amidinohydrocinnamoyl)glycyl]-3-(t-butoxycarbonyl)-L-alanyl]amino]cyclopentanecarboxylic acid there are obtained, after crystallization, 15 mg of 1-[[N-[N-(p-amidinohydrocinnamoyl)glycyl]-L-α-aspartyl]amino] cyclopentanecarboxylic acid trifluoroacetate (1:1), m.p. 136°–138° C. (ether, decomposition).

The starting material can be prepared as follows:

a) Analogously to Example 1B)e), from 761 mg of Z-Gly-Asp(OtBu)-OH (Example 16) and 359 mg of 1-aminocyclopentanecarboxylic acid methyl ester hydrochloride in tetrahydrofuran there are obtained, after chromatography on silica gel with ethyl acetate, 920 mg of N-[N-benzyloxycarbonylglycyl]-3-[[1-(methoxycarbonyl)cyclopentyl]carbamoyl]-β-alanine t-butyl ester, MS (FAB): 506 (M+1)$^+$.

b) By hydrogenolysis analogously to Example 1B)b) there are obtained from 880 mg of the product of the previous step 620 mg of 1-[[3-(t-butoxycarbonyl)-N-glycyl-L-alanyl]amino]cyclopentanecarboxylic acid methyl ester, MS (FAB): 372 (M+1)$^+$.

c) Analogously to Example 1B)e), by coupling 310 mg of 3-(p-cyanophenyl)propionic acid and 600 mg of the product of the previous step there are obtained, after chromatographic purification (silica gel; ethyl acetate-ethyl acetate/methanol 9:1), 635 mg of 1-[[3-(t-butoxycarbonyl)-N-[N-(p-cyanohydrocinnamoyl) glycyl]-L-alanyl]amino]cyclopentanecarboxylic acid methyl ester, MS: 546 (M+NH$_4$)$^+$.

d) Analogously to Examples 1Bf)g)h), by the successive reaction of 600 mg of the product of the precious step with H$_2$S, MeI and ammonium acetate there are obtained 279 mg of 1-[[N-[N-(p-amidinohydrocinnamoyl)glycyl]-3-(t-butoxycarbonyl)-L-alanyl]amino]cyclopentanecarboxylic acid methyl ester hydroiodide, m.p.98° C. (decomposition), MS (FAB): 546 (M+1)$^+$.

e) Alkaline hydrolysis of 157 mg of the product of the previous step as described in Example 16B)b) yields 24 mg of 1-[[N-[N-(p-amidinohydrocinnamoyl)glycyl]-3-(t-butoxycarbonyl)-L-alanyl]amino] cyclopentanecarboxylic acid, m.p. 163°–164° C.

EXAMPLE 34

A solution of 275.5 mg of N-Boc-3-(4-aminophenyl)-DL-alanyl-Gly-Asp-Val-OH (Example 15B)d)) in 3 ml of H$_2$O is adjusted to pH 9.5 with 1N NaOH. This solution is treated with 219 mg of methyl acetimidate.HCl and the pH value is again adjusted to 9.5 with 1N HCl. After stirring for 2 hours the reaction mixture is acidified to pH 4 with 1N HCl and chromatographed on a Sephadex G-25S column in 0.2N acetic acid. The main fraction is lyophilized and purified on Lichrosorb RP18 with 0.05M ammonium acetate ethanol. The uniform fraction is lyophilized from water. There are obtained 25 mg of [3-[p-(acetimidoylamino)phenyl]-N-(t-butoxycarbonyl)-DL-alanyl]-Gly-Asp-Val-OH, MS: 593 (M+H)$^+$.

EXAMPLE A

A compound of formula I can be used in a manner known per se as the active ingredient for the manufacture of tablets of the following composition:

|  | Per tablet |
| --- | --- |
| Active ingredient | 200 mg |
| Microcrystalline cellulose | 155 mg |
| Maize starch | 25 mg |
| Talc | 25 mg |
| Hydroxypropylmethylcellulose | 20 mg |
|  | 425 mg |

EXAMPLE B

A compound of formula I can be used in a manner known per se as the active ingredient for the manufacture of capsules of the following composition:

|  | Per capsule |
| --- | --- |
| Active ingredient | 100.0 mg |
| Maize starch | 20.0 mg |
| Lactose | 95.0 mg |
| Talc | 4.5 mg |
| Magnesium stearate | 0.5 mg |
|  | 220.0 mg |

What is claimed is:

1. A compound of the formula

wherein

R is a group selected from the group consisting of
$R^b$—NH—(CH$_2$)$_p$—CH(NH—$R^a$)—,
$R^c$—NHCH$_2$—C$_6$H$_4$—(T)$_r$—, L—C(NH)—(NH)$_n$—C$_6$H$_4$—(T)— and

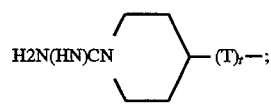

$R^a$ is selected from the group consisting of hydrogen, —COO—(C$_m$-alkyl), Z, —COC$_6$H$_5$, —COC$_6$H$_4$N$_3$, —SO$_2$-napthyl and —COCH$_2$N(Y)—CH$_2$CH$_2$NH—Y;

Y is selected from the group consisting of hydrogen, Boc and Z;

$R^b$ is a group of the formula —C(NH)(CH$_2$)$_q$—CH$_3$, amidino or

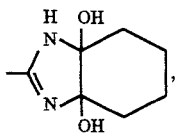

with the proviso that $R^b$ can be amidino only if $R^a$ is one of —COC$_6$H$_4$N$_3$, SO$_2$-napthyl or —COCH$_2$N(Y)—CH$_2$CH$_2$NH—Y;

$R^c$ is hydrogen or amidino;

n is 1 or 0;

t is 1 or 0;

L is amino or, when n is 1, L is amino or —(CH$_2$)$_q$—CH$_3$,

T is a group selected from the group consisting of the formula —(O)$_r$—CH$_2$—, —CH=CH—, —CH$_2$CH(R$^d$)— and —C(O)CH$_2$—, wherein a carbonyl group present in the group T can instead be present as a ketal;

$R^d$ is hydrogen or —NH—$R^a$;

R' is hydrogen or —CO—$R^o$;

$R^o$ is selected from the group consisting of amino, —NH—(C$_m$-alkyl), —NH(CH$_2$)$_m$—C$_6$H$_5$, —NH(CH$_2$)$_m$—C$_6$H$_4$-Hal, —NH—C$_6$H$_4$—COOH, —NH—C$_6$H$_4$—COO—C$_m$-alkyl, and an α-aminocarboxylic acid group attached via the amino group;

m is 1–4;

p is 1–6;

q is 0–3;

r is 1 or 0;

or a hydrate or solvate or a physiologically acceptable salt thereof.

2. The compound of claim 1, wherein R is a group selected from the group consisting of $R^b$—NH—(CH$_2$)$_p$—CH(NH—$R^a$)—, $R^c$—NHCH$_2$—C$_6$H$_4$—(T)$_r$— and L—C(NH)—(NH)$_n$—C$_6$H$_4$—(T)$_r$, wherein L is amino, and T is selected from the group consisting of —(O)$_r$—CH$_2$—, —CH=CH— and —CH$_2$CH(R$^d$)—.

3. The compound of claim 1, wherein R is a group of the formula L—C(NH)—(NH)$_n$—C$_6$H$^4$—(T)$_r$—;

L is amino;

n is 0;

t is 1;

T is selected from the group consisting of —(O)$_r$—CH$_2$—, —CH$_2$CH(R$^d$)— and —C(O)CH$_2$, in which the group C(O) can instead be present as a ketal;

r is 1 or 0;

$R^d$ is hydrogen or —NH-$R^a$;

$R^a$ is selected from the group consisting of hydrogen, a group —COO—(C$_m$-alkyl), and the group Z;

R' is hydrogen or —C(O)—$R^o$;

$R^o$ is selected from the group consisting of —NH—(C$_m$-alkyl), —NH(CH$_2$)$_m$—C$_6$H$_4$-Hal, —NH—C$_6$H$_4$—COOH and an α-amino-carboxylic acid group attached via the amino group.

4. The compound of claim 2, wherein R is a group of the formula $R^c$—NHCH$_2$—C$_6$H$_4$—(T)$_r$—.

5. The compound of claim 3, wherein $R^d$ is —NH—$R^a$, and $R^a$ is a group COO—(C$_m$-alkyl).

6. The compound of claim 3, wherein said α-amino-carboxilic acid group is selected from the group consisting of -Val-OH, -Ser-OH, -Nal-OH, -Phe-OH and —NH-1,1-cyclopentane-COOH, wherein Nal is —NH-(1-napthyl) ethylidene-COOH.

7. The compound of claim 3, wherein T is CH$_2$.

8. The compound of claim 4, wherein R—CO is p-(aminomethyl)hydrocinnamoyl.

9. The compound of claim 4, wherein R' is selected from the group consisting of hydrogen, —CO-Val-OH, —CO-Ser-OH, —CO-Phe-OH, 1-carboxy-2-(1-napthyl) ethylidenecarbamoyl, —CO-Ile-OH, carboxyphenylcarbamoyl, isobutycarbamoyl and p-fluorophenethylcarbamoyl.

10. The compound of claim 5, wherein $R^a$ is Boc.

11. The compound of claim 7, wherein the compound is (p-amidinophenyl)acetyl-Gly-Asp-Val.

12. The compound of claim 2, wherein R is a group of the formula $R^b$—NH—(CH$_2$)$_p$—CH(NH.R$^a$)—, and R—CO is selected from the group consisting of Aeg-Arg-, Z-Aeg(Z)-Arg-, 2-napthyl-SO$_2$-Arg-, o-azidobenzoyl-Arg-, N$_2$-Boc-N$_6$-(1-imino-ethyl)-Lys- and N$_2$-Boc-N$_5$-(3a,4,5,6,7,7a-hexahydro-3a,7a-dihydroxy-1H-benzimidazol-2-yl)-Orn.

13. The compound of claim 1, wherein R is a group of the formula

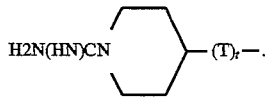

14. The compound of claim 1, wherein R—CO— is 3-(1-amidino-4-piperidinyl)propionyl.

15. The compound of claim 1, wherein R is a group of the formula L—C(NH—(NH)$_n$—C$_6$H$_4$—(T)$_r$—, and R—CO— is selected from the group consisting of p-amidinohydrocinnamoyl, 3-(p-amidinophenyl)alanyl, 3-(p-guanidinophenyl)alanyl, N-Z-3-(p-amidinophenyl) alanyl, N-Boc-3-(p-amidinophenyl)alanyl, N-Boc-3-(p-guanidinophenyl)alanyl, p-amidinophenoxyacetyl, p-amidinophenacetyl, 2-((p-amidinophenyl)-1,3-dioxolan-2-yl)acetyl, (p-amidinobenzoyl)acetyl and N-Boc-3-(p-acetimidoylaminophenyl)alanyl.

16. The compound of claim 1, wherein R' is selected from the group consisting of hydrogen, —CO-Val-OH, —CO-Ser-OH, —CO-Phe-OH, 1-carboxy-2-(1-napthyl) ethylidenecarbamoyl, —CO-Ile-OH, carboxyphenylcarbamoyl, isobutylcarbamoyl and p-fluorophenethylcarbamoyl.

17. The compound of claim 12, wherein R' is selected from the group consisting of hydrogen, —CO-Val-OH, —CO-Ser-OH, —CO-Phe-OH, 1-carboxy-2-(1-napthyl) ethylidenecarbamoyl, —CO-Ile-OH, carboxyphenylcarbamoyl, isobutylcarbamoyl and p-fluorophenethylcarbamoyl.

18. The compound of claim 13, wherein R' is selected from the group consisting of hydrogen, —CO-Val-OH, —CO-Ser-OH, —CO-Phe-OH, 1-carboxy-2-(1-napthyl) ethylidenecarbamoyl, —CO-Ile-OH, carboxyphenylcarbamoyl, isobutylcarbamoyl and p-fluorophenethylcarbamoyl.

19. The compound of claim 2, selected from the group consisting of (3-(p-Amidinophenyl)-DL-alanyl)-Gly-Asp-Val-OH,
Z-Aeg(Z)-Arg-Gly-Asp-Val-OH,
Aeg-Arg-Gly-Asp-Val-OH,
Aeg-Arg-Gly-Asp-Ser-OH,
N-Aeg-Arg-Gly-Asp-Nal(1)-OH,
Aeg-Arg-Gly-Asp-Ile-OH,
(N$_2$-Boc-N$_6$-(1-iminoethyl)-L-lysyl)-Gly-Asp-Val-OH,
N-((o-azidobenzoyl)-Arg-Gly-Asp)-anthranilic acid, ($N_2$-Boc-$N_5$-(3a,4,5,6,7,7,a-hexahydro-3a,7a-dihydroxy-1H-benzimidazol-2-yl)-L-ornithyl-Gly-Asp-Val-OH,
(N-Boc-3-(p-guanidinophenyl)-DL-alanyl)-Gly-Asp-Val-OH,
(3-(p-amidinophenyl)-DL-alanyl)-Gly-Asp-Nal(1)-OH,
(N-Boc-3-(p-amidinophenyl)-DL-alanyl)-Gly-Asp-Val-OH,
(p-amidinohydrocinnamoyl)-Gly-Asp-Nal(1)-OH,
(3-(p-amidinophenyl-D-alanyl)-Gly-Asp-Val-OH,
(p-aminomethylhydrocinnamoyl)-Gly-Asp-Val-OH,
(p-amidinohydrocinnamoyl)-Gly-Asp-Val-OH,
(3-(p-amidinophenyl)-L-alanyl)-Gly-Asp-Val-OH,
(p-amidinophenoxy)acetyl-Gly-Asp-Val-OH and
(p-amidinophenyl)acetyl-Gly-Asp-Val-OH.

20. A pharmaceutical composition comprising the compound of claim 1 together with a pharmaceutically acceptable carrier.

21. A method of treating or inhibiting thrombosis in a mammal comprising administering a compound of claim 1 to a mammal in need thereof.

* * * * *

UNITED STATES PATENT AND TRADEMARK OFFICE
CERTIFICATE OF CORRECTION

PATENT NO. : 5,663,297  Page 1 of 2

DATED : September 2, 1997

INVENTOR(S) : Leo Alig, Albrecht Edenhofer, Marcel Müller, Arnold Trzeciak, Thomas Weller It is certified that error appears in the above-indentified patent and that said Letters Patent is hereby corrected as shown below:

In claim 1, column 24, line 49, please replace "R-CONH-$CH_2$-CONH-CH(R').$CH_2$COOH" with -- R-CONH-$CH_2$-CONH-CH(R')-$CH_2$COOH --.

In claim 1, column 24, line 55, please replace "L-C(NH)-$(NH)_n$-$C_6H_4$-(T)-" with -- L-C(NH)-$(NH)_n$-$C_6H_4$-$(T)_t$- --.

In claim 3, column 25, line 44, please replace "L-C(NH)-$(NH)_n$-$C_6H^4$-$(T)_t$-" with -- L-C(NH)-$(NH)_n$-$C_6H_4$-$(T)_t$- --.

In claim 6, column 25, line 66, please replace "carboxilic" with -- carboxylic --.

In claim 9, column 26, line 10, please replace "isobutycarbamoyl" with -- isobutylcarbamoyl --.

In claim 12, column 26, line 16, please replace "$R^b$-NH-$(CH_2)_p$-CH(NH.$R^a$)-" with -- $R^b$-NH-$(CH_2)_p$-CH(NH-$R^a$)- --.

In claim 15, column 26, line 31, please replace "L-C(NH-$(NH)_n$-$C_6H_4$-$(T)_t$-" with -- L-C(NH)-$(NH)_n$-$C_6H_4$-$(T)_t$- --.

UNITED STATES PATENT AND TRADEMARK OFFICE
CERTIFICATE OF CORRECTION

PATENT NO. : 5,663,297
DATED : September 2, 1997
INVENTOR(S) : Leo Alig, Albrecht Edenhofer, Marcel Müller, Arnold Trzeciak, Thomas Weller It is certified that error appears in the above-indentified patent and that said Letters Patent is hereby corrected as shown below:

In claim 19, column 27, line 1, please replace "($N_2$-Boc-$N_5$-(3a,4,5,6,7,7,a-hexahydro-3a,7a-dihydroxy-1H-benzimidazol-2-yl)-L-ornithyl-Gly-Asp-Val-OH," with -- ($N_2$-Boc-$N_5$-(3a,4,5,6,7,7a-hexahydro-3a,7a-dihydroxy-1H-benzimidazol-2-yl)-L-ornithyl-Gly-Asp-Val-OH, --.

Signed and Sealed this

Twenty-fifth Day of November, 1997

Attest:

BRUCE LEHMAN

*Attesting Officer*    *Commissioner of Patents and Trademarks*